(12) United States Patent
Phillips

(10) Patent No.: US 6,221,026 B1
(45) Date of Patent: Apr. 24, 2001

(54) BREATH TEST FOR THE DETECTION OF VARIOUS DISEASES

(76) Inventor: Michael Phillips, 1 Horizon Rd., Fort Lee, NJ (US) 07024

(*) Notice: Subject to any disclaimer, the term of this patent is extended or adjusted under 35 U.S.C. 154(b) by 0 days.

(21) Appl. No.: 09/229,020

(22) Filed: Jan. 12, 1999

(51) Int. Cl.[7] .................................................. A61B 5/08

(52) U.S. Cl. ........................ 600/532; 128/898; 600/529

(58) Field of Search ........................... 600/529, 532–533, 600/537–538, 540–541, 543, 300; 128/898

(56) References Cited

U.S. PATENT DOCUMENTS 5,465,728  11/1995  Phillips .

OTHER PUBLICATIONS

Phillips M., Breath Tests in Medicine, Scienctific American 1992; 267(1):74–79.
Phillips M,. Sabas M., & Greenberg J., Alveolar Gradient of Pentane in Normal Human Breath, Free Radical Res. Commun. 1994; 20:333–337.
Phillips, M., Method for the Collection and Assay of volatile organic compounds in breath, Analytical Biochemistry 1997;247:272–278.
Phillips, M. and Greenberg J., Detection of Endogenous Ethanol and Other Compounds in the Breath by gas chromatography with on–column concentration of sample, Analytical Biochemistry, 1987;163:165–169.

Primary Examiner—Cary O'Connor
Assistant Examiner—Ryan Carter
(74) Attorney, Agent, or Firm—Pitney, Hardin, Kipp & Szuch, LLP

(57) ABSTRACT

The alkane profile, comprising the alveolar gradients of n-alkanes in breath having 4 to 20 carbons, is determined for the diagnosis of disease in mammals, including humans.

10 Claims, 18 Drawing Sheets

BREATH TEST FOR THE DETECTION OF VARIOUS DISEASES

BACKGROUND OF THE INVENTION

1. Field of the Invention

The invention relates to the diagnosis of disease in mammals and more particularly to a method employing breath testing for the detection of particular diseases in humans.

2. Brief Description of Related Art

Volatile Organic Compounds in Human Breath

Alveolar breath is a distinctive gas whose chemical composition differs markedly from inspired air. Volatile organic compounds (VOCs) are either subtracted from inspired air (by degradation and/or excretion in the body) or added to alveolar breath as products of metabolism. Some features of this transformation have been well understood for many years: e.g. oxygen is subtracted and carbon dioxide is added by the oxidative metabolism of glucose (Phillips M., Breath tests in medicine, Scientific American 1992:267(1):74–79).

Pauling et al, in 1971, employed cold trapping to concentrate the VOCs in breath and found that normal human breath contained several hundred different VOCs in low concentrations (Pauling L. Robinson AB, Teranishi R and Cary P: Quantitative analysis of urine vapor and breath by gas-liquid partition chromatography, Proc Nat Acad Sci USA 1971:68:2374–6). This observation has been subsequently confirmed in many different laboratories, employing progressively more sophisticated and sensitive assays. More than a thousand different VOCs have been observed in low concentrations in normal human breath (Phillips M: Method for the collection and assay of volatile organic compounds in breath, Analytical Biochemistry 1997; 247:272–278).

Breath Alkanes as Markers of Disease

Analysis of VOCs in inspired air and alveolar breath is a useful research tool with potential applications in clinical medicine. Breath analysis opens a non-invasive window on normal metabolic pathways, and also illustrates how these pathways are altered in disease.

Figure 5:
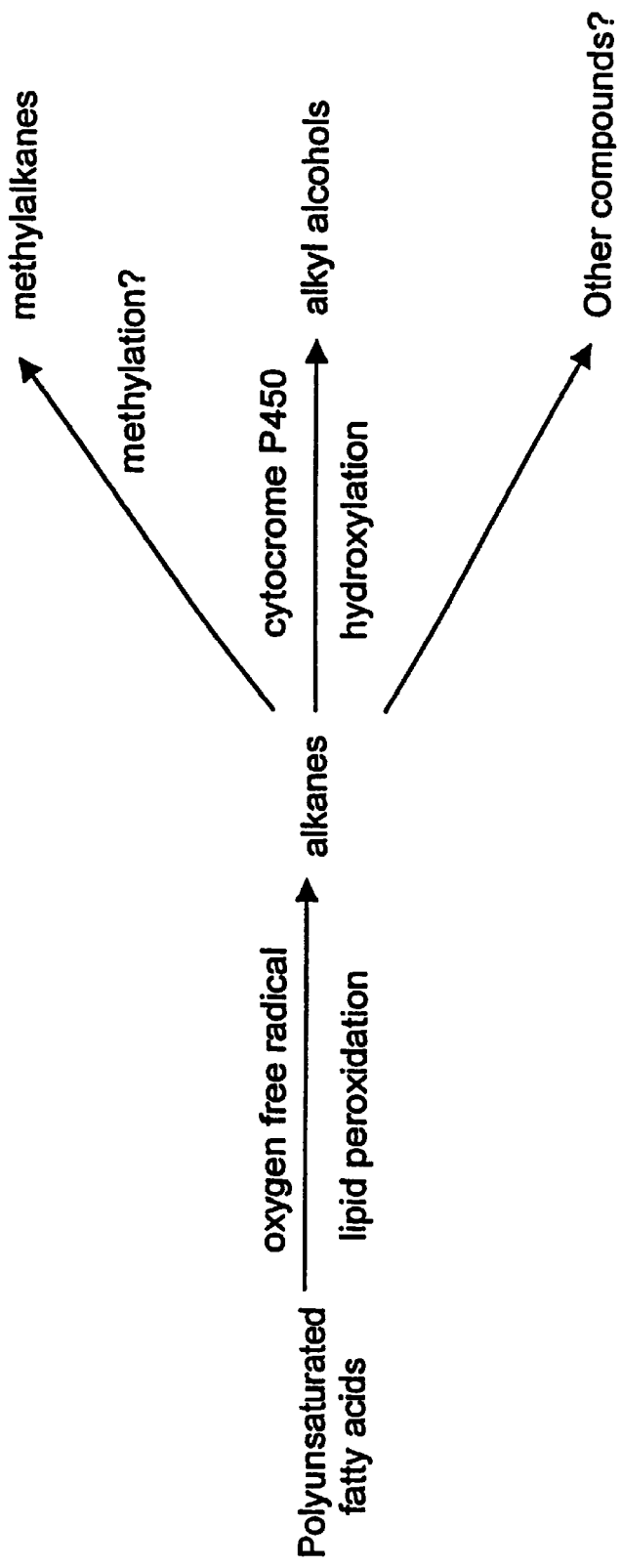

Alkanes in breath are markers of oxygen free radical (OFR) activity in vivo. OFRs degrade biological membranes by lipid peroxidation, converting polyunsaturated fatty acids (PUFAs) to alkanes which are excreted through the lungs as volatile organic compounds (VOCs); (Kneepkens CMF, Ferreira C. Lepage G and Roy C C: The hydrocarbon breath test in the study of lipid peroxidation; principles and practice, Clin Invest Med 1992; 15(2):163–186; Kneepkens C M F, Lepage G and Roy C C: The potential of the hydrocarbon breath test as a measure of lipid peroxidation, Free Radic Biol Med 1994; 17:127–60) (FIG. 5). Increased pentane in the breath has been reported as a marker of oxidative stress in several diseases including breast cancer (Hietanen E, Bartsch H, Beireziat J-C, Camus A-M, McClinton S. Eremin O, Davidson L and Boyle P: Diet and oxidative stress in breast, colon and prostate cancer patients: a case control study, European Journal of Clinical Nutrition 1994; 48:575–586), heart transplant rejection (Sobotka P A, Gupta D K, Lansky D M, Costanzo M R and Zarling E J: Breath pentane is a marker of acute cardiac allograft rejection. J. Heart Lung Transplant 1994; 13:224–9), acute myocardial infarction (Weitz Z W, Birnbaum A J, Sobotka P A, Zarling E J and Skosey J L: High breath pentane concentrations during acute myocardial infarction. Lancet 1991; 337:933–35), schizophrenia (Kovaleva E. S, Orlov O. N, Tsutsul'kovskaia Mia, Vladimirova T. V, Beliaev B. S: Lipid peroxidation processes in patients with schizophrenia. Zh Nevropatol Psikiatr 1989:89(5): 108–10), rheumatoid arthritis (Humad S. Zarling E. Clapper M and Skosey J L: Breath pentane excretion as a marker of disease activity in rheumatoid arthritis, Free Rad Res Comms 198; 5(2):101–106) and bronchial asthma (Olopade C O, Zakkar M, Swedler W I and Rubinstein I: Exhaled pentane levels in acute asthma, Chest 1997; 111(4):862–5). Analysis of breath alkanes could potentially provide a new and non-invasive method for early detection of some of these disorders (Phillips M: Breath tests in medicine, Scientific American 1992; 267(1):74–79).

Alkanes are degraded to other VOCs such as alkyl alcohols and possibly to methyl alkanes (Phillips M: Method for the collection and assay of volatile organic compounds in breath, Analytical Biochemistry 1997; 247:272–78) but there is little information about the excretion of these compounds in the breath, where they might also provide clinically useful markers of disease.

Breath testing for VOC markers of oxidative stress is a comparatively new field of research, and published information is scanty in a number of areas: First, studies of breath alkanes have focused near-exclusively on ethane and pentane which are degradation products of n-3 and n-6 PUFAs respectively. Hexane and octane have also been observed in the breath of animals, but there is little information about longer chain VOCs in normal human breath. Second, most studies have taken little or no account of the presence of alkanes in the inspired ambient air, where they appear to be near-universal contaminants. Cailleux and Allain questioned whether pentane was a normal constituent of human breath, because the concentrations in breath and inspired air, were frequently so similar. (Cailleux A & Allain P: Free Radicals Res Commun 1993; 18:323–327). This problem may be resolved by determination of the alveolar gradient of a VOC, the difference between its concentration in the breath and in the ambient air. (Phillips M. Sabas M. & Greenberg J: Free Radical Res Commun 1994; 20:333–337).

Breath Alkanes as Markers of Breast Cancer

Breast cancer is a common disease which now affects approximately one in every ten women in the United States. Early detection by periodic screening mammography can reduce mortality by 20–30%. However, mammography is expensive, frequently requires painful breast compression, entails exposure to radiation, and generates false-positive results in one third of all women screened over a 10 year period (Elmore J G, Barton M B, Moceri V M, Polk S, Arena P J and Fletcher S W: Ten-year risk of false positive screening mammograms and clinical breast examinations). There is a clinical need for a screening test for breast cancer which is at least as sensitive and specific as mammography, but is simpler, safer, less painful and less expensive.

The cytochrome P450 (CYP) system comprises a group of mixed function oxidase enzymes which metabolize drugs and other xenobiotics. This system also metabolizes alkanes to alcohols e.g. n-hexane to 2- and 3-hexanol (Crosbie S J, Blain P G and Williams F M: Metabolism of n-hexane by rat liver and extrahepatic tissues and the effect of cytochrome P-40 inducers. Hum Exp Toxicol 1997; 16(3):131–137).

Rats treated with a potent cytochrome P-450 inhibitor exhibited a ten-fold increase in hexane and other breath VOCs with no increase in hepatic lipid peroxidation, demonstrating the significance of this pathway for VOC clearance (Mathews J M, Raymer J H, Etheridge A S, Velez Gr and Bucher J R: Do endogenous volatile organic chemicals in breath reflect and maintain CYP2E1 levels in vivo? Toxicol Appl Pharmacol 1997; 146(2):255–60). Studies in normal animals initially have demonstrated that the liver is a major site of clearance of alkanes from the body by cytochrome P450 metabolism (Burk-R J; Ludden-T M; Lane-J M: Pentane clearance from inspired air by the rat: dependence on the liver. Gastroenterology. 1983 84(1): 138–42: Daugherty-M S; Ludden-T M; Burk-R F: Metabolism of ethane and pentane to carbon dioxide by the rat, Drug-Metab-Dispos. 1988; 16(5):666–71).

However, several recent reports have demonstrated that cytochrome P450 metabolism is not confined to the liver. Metabolism of alkanes to alcohols has also been observed in lung, brain and skeletal muscle microsomes expressing cytochrome P450 2E1 or 2B6 (Crosbie S J, Blain P G and Williams F M: Metabolism of n-hexane by rat liver and extrahepatic tissues and the effect of cytochrome P-450 inducers. Hum Exp Toxicol 1997; 16(3):131–137). The cytochrome P450 system is also present in human breast tissue. Murray et al reported that cytochrome P450 CYP1 B1 was expressed in cancers of breast as well as other tissues (Murray G I, Taylor M C, McFadyen M C, McKay J A, Greenlee W F, Burke M D and Melvin W T: Tumor-specific expression of cytochrome P450 CYP1B1. Cancer Res 1997; 57(14):3026–31). Huang et al detected activity of the xenobiotic-metabolizing CYP1, CYP2 and CYP3 subfamilies of cytochrome P450 in human breast tissue (Huang Z, Fasco M J, Figge H L, Keyomarsi K and Kaminsky L S: Expression of cytochromes P450 in human breast tissue and tumors. Drug Metab Dispos 1996; 24(8):599–905). They observed: " . . . . When normal and tumor tissues were from the same individuals, higher amplification occurred in normal tissues . . . . The machinery of possible in situ bioactivation of xenobiotics and modification of therapeutic drugs is thus present in human breast tissue". Taken together, these studies demonstrate:

1. Alkanes are metabolized in vivo by cytochrome P450 enzymes
2. Cytochrome P450 enzymes are present in normal and neoplastic human breast tissues
3. Breast cancer induces increased cytochrome P450 activity in normal breast tissue
4. Breast cancer may therefore induce increased metabolism of alkanes.

Hietanen et al studied 20 women with histologically proven breast cancer and a group of age and sex-matched controls (Hietanen E, Bartsch H, Beireziat J-C, Camus A-M, McClinton S. Eremin O, Davidson L and Boyle P: Diet and oxidative stress in breast, colon and prostate cancer patients: a case control study, European Journal of Clinical Nutrition 1994; 48:575–586). Mean breath pentane concentration in the cancer patients (2.6 ppb, SD=2.8) was significantly higher than in the controls (0.6 ppb, SD=1.1, p<0.01). They did not report concentrations of pentane in ambient air, nor the alveolar gradients of pentane.

Breath Alkanes as Markers of Ischemic Heart Disease

More than 3 million patients are hospitalized every year in the United States for chest pain. The cost is over $3 billion just for those found to be free of acute disease. Many patients with acute chest pain but without myocardial infarction are admitted to specialized services to determine the cause of their pain (Hoekstra J W and Gibler W B; Chest pain evaluation units: an idea whose time has come, JAMA 1997; 278(20):1701–2). The main objective is to detect unstable angina, which is potentially life threatening. Evaluation of these patients is frequently extensive and expensive, entailing a comprehensive battery of tests such as echocardiography, exercise electrocardiography (ECG), myocardial scintigraphy and Holter monitoring. Employing such a battery of tests, Fruergaard et al evaluated 204 patients with acute chest pain but without myocardial infarction. They found the commonest etiology was gastro-esophageal disease, followed by ischemic heart disease and chest wall syndrome. The high risk subset comprised less than a third of all diagnoses (Fruergaard P, Laundbjerg J, Hesse B et al: The diagnoses of patients admitted with acute chest pain but without acute myocardial infarction. Eur Heart J 1996; 17(7):1028–34). McCullough et al determined that the practice of hospital admission for patients with chest pain and essentially normal ECGs was not cost favorable, at. $1.7 million dollars per life saved (McCullough P A, Ayad O, O'Neill W W and Goldstein J A: Costs and outcomes of patients admitted with chest pain and essentially normal electrocardiograms. Clin Cardiol 1988; 21(1):22–6). Despite these and other well-documented studies, patients with acute chest pain but without myocardial infarction are commonly hospitalized because physicians are generally reluctant to discharge a patient if there is a risk of unstable angina and sudden death. Hence there is a clinical need and an economic need for a diagnostic test which differentiates between the high-risk patient with cardiac chest pain who could benefit from hospitalization, and the low-risk patient with non-cardiac chest pain who could be safely discharged home and evaluated as an out-patient. Such a test could potentially reduce mortality and morbidity from unrecognized heart disease, while at the same time reducing costs to the health care system by reducing the number of unnecessary hospitalizations. There is now new evidence that a non-invasive breath test could provide such a test.

There is an increasing body of evidence that myocardial oxygen free radical activity is increased in ischemic heart disease. Oxidative stress also increases during surgical reperfusion of the heart, or after thrombolysis, and it is related to transient left ventricular dysfunction, or stunning (Ferrari R; Agnoletti L; Comini L; Gaia G; Bachetti T; Cargnoni A; Ceconi C; Curello S; Visioli O; Oxidative stress during myocardial ischaemia and heart failure, Eur Heart J 1998; 19 Suppl B:B2-11). The two major hypotheses which explain the mechanism of stunning are that it either results from a burst of oxygen free radical activity or from a loss of sensitivity of contractile filaments to calcium. These hypotheses are not mutually exclusive, and are likely to represent different facets of the same pathophysiological cascade. Myocardial stunning occurs clinically in various situations in which the heart is exposed to transient ischemia, such as unstable angina, acute myocardial infarction with early reperfusion, exercised-induced ischemia, cardiac surgery and cardiac transplantation (Bolli R: Basic and clinical aspects of myocardial stunning, Prog Cardiovasc Dis 1998; 40(6): 477–516:

Miura H; Morgan D A; Gutterman D D; Oxygen-derived free radicals contribute to neural stunning in the canine heart, Am J Physiol 1997; 273(3 Pt 2): H1569–75).

In 1991, Weitz et al reported that breath pentane was significantly increased in 10 patients with acute myocardial infarction compared to 10 healthy controls (Weitz Z W, Birnbaum A J, Sobotka P A, Zarling E J and Skosey J L: High breath pentane concentrations during acute myocardial infarction. Lancet 1991; 337:933–35). However, these results were called into question by a subsequent study from the same institution which found no significant differences in breath pentane between 15 patients with acute myocardial infarction, 15 with stable angina and 15 normal controls (Mendis S. Sobotka P A and Euler D E: Expired hydrocarbons in patients with acute myocardial infarction, Free Radic Res 1995; 23(2):117–22). They did observe a significant increase in breath pentane following balloon deflation in five patients with unstable angina undergoing coronary angioplasty (Mendis S, Sobotka P A, Leja F L and Euler D E: Breath pentane and plasma lipid peroxides in ischemic heart disease, Free Radic Biol Med 1995; 19(5):679–84). However, Kohlmuller and Kochen demonstrated a fundamental flaw in the breath pentane assays: the column employed in the gas chromatograph (GC) did not separate pentane from isoprene, the most abundant compound in breath. What the investigators had reported as breath pentane was probably a mixture of pentane and isoprene (Kohlmuller D; Kochen W: Is n-pentane really an index of lipid peroxidation in humans and animals? A methodological reevaluation. Anal Biochem 1993 May 1; 210(2):268–76). The GC columns employed in this research separate pentane and isoprene from one another (Phillips M, Sabas M and Greenberg J: Alveolar gradient of pentane in normal human breath. Free Radical Research Communications 1994; 20(5):333–337).

Breath Alkanes as Markers of Heart Transplant Rejection

In December 1967, Christiaan Barnard, a South African surgeon, performed the first human heart transplant. Three days later, a surgical team in Brooklyn performed the first heart transplant in the United States. Since then, more than 36,000 heart transplants have been performed at over 271 centers throughout the world, including approximately 165 centers in the United States. There are nearly 20,000 people alive today in the United States who are the recipients of transplanted hearts. Refinements in patient selection, improved surgical techniques, newer antimicrobial agents, better myocardial protection, and the application of right ventricular endomyocardial biopsy to identify allograft rejection have resulted in better overall survival rates. Nevertheless, the most significant change in the management of transplant recipients came with the introduction and widespread commercial availability of cyclosporine in the early 1980s. Today, overall one year survival exceeds 80% and reported five and ten year survival approaches 65–70%.

With the introduction of cyclosporine in the early 1980s, the incidence of life threatening acute allograft rejection decreased considerably. Unfortunately, patients receiving cyclosporine based triple drug immunosuppression regimens seldom have physical complaints suggestive of allograft rejection until very late in the rejection process. Even prior to the introduction of cyclosporine, however, signs and symptoms of allograft rejection were quite nonspecific; generally ranging from subtle electrocardiographic changes to malaise, fatigue, dyspnea, edema, and anorexia (Winters G L, Loh E, Schoen F J: Natural history of focal moderate cardiac allograft rejection, Circulation 1995; 91:1975. Billingham M E, Cary N R B, Hammond E H et al: A working formulation for the standardization of nomenclature in the diagnosis of heart and lung rejection. heart rejection study group. Heart Transplant 1990; 9:587). Non-invasive techniques to diagnose rejection, such as electrocardiographic changes or echocardiographic indices suggestive of diastolic dysfunction, are relatively insensitive and have not routinely been used in clinical practice. Likewise, thallium and magnetic resonance imaging have not proven useful. Hence, right ventricular endomyocardial biopsy has remained the standard against which all other techniques are compared. The primary purposes of the right ventricular endomyocardial biopsy in the heart transplant recipient are to identify allograft rejection, assess the efficacy of treatment, and to rule out infectious etiologies. Biopsies are performed weekly for the first six post-operative weeks, biweekly until the third post-operative month, and monthly until month six. Subsequent intervals are generally determined on an individual basis. Unfortunately, right ventricular endomyocardial biopsy is associated, albeit infrequently, with complications including hematoma, infection, arrhythmia, ventricular perforation, and the development of coronary artery to right ventricle fistulas. There is a clinical need for an alternative method of detecting heart transplant rejection with a safe and non-invasive diagnostic test.

There is a well-documented biochemical basis for breath testing provides for the early detection of transplant rejection. Tissue damage arising from inflammation is accompanied by an accumulation of intracellular oxygen free radicals (OFRs) which cause lipid peroxidation of lipid membranes (Kneepkens C M F, Ferreira C, Lepage G and Roy C C: The hydrocarbon breath test in the study of lipid peroxidation: principles and practice. Clin Invest Med 1992; 15(2):163–186. Kneepkens C M F, Lepage G, Roy C C. The potential of the hydrocarbon breath test as a measure of lipid peroxidation. Free Radic Biol Med 1994; 17:127–60). This process is accompanied by the evolution of alkanes which are excreted in the breath. One of these alkanes, pentane, is the best documented marker of OFR activity. Sobotka et al studied 37 outpatients with stable cardiac allograft function. (Sobotka P A, Gupta D K, Lansky D M, Costanzo M R and Zarling E J: Breath pentane is a marker of acute cardiac allograft rejection. J Heart Lung Transplant 1994; 13:224–9). Breath pentane was measured by gas chromatography and the results were compared with routine surveillance endomyocardial biopsy. Histopathologic findings consistent with rejection were present on endomyocardial biopsy in 52% of the subjects. Average pentane excretion for subjects with mild rejection (4.2 nmol/l, SD=2.8) or moderate rejection (5.4 nmol/l, SD=2.6) exceeded that seen in subjects who did not have rejection (1.7 nmol/l, SD=0.9) ($p<0.02$). A pentane cutoff value of 2.43 nmol/l, chosen to give the highest negative predictive value, had a sensitivity of 0.80. The authors concluded that breath pentane excretion was a sensitive noninvasive screening test for the detection of cardiac allograft rejection. These encouraging results have attracted criticism: Holt et al noted that the details of their analytic technique were sketchy; they may not have really been observing isoprene because most chromatographic columns do not separate pentane from isoprene, the most abundant compound in human breath. (Holt D W, Johnston A and Ramsey J D: Breath pentane and heart rejection. J Heart Lung Transplant 1994; 13:1147–8. Kohlmuller D, Kochen W: Is n-pentane really an index of lipid peroxidation in humans and animals? A methodological reevaluation. Anal Biochem 1993; 210:266–76).

SUMMARY OF THE INVENTION

Improved analytical technology was employed to determine the most abundant volatile organic compounds (VOCs) in the breath of 50 normal humans.

Kinetic analysis was employed to demonstrate that the alveolar gradient of a VOC (abundance in breath minus abundance in room air) varies with the difference between the rate at which a VOC is synthesized in the body and the rate at which it is cleared from the body by metabolism and excretion.

A new marker of oxygen free radical (OFR) activity in the body was developed: the breath alkane profile. This comprised the alveolar gradients of a wide spectrum of VOCs ranging from C2 to C20 alkanes plotted as a function of carbon chain length. Similar profiles were developed for two alkane metabolites in breath: alkyl alcohols and 2-methyl alkanes. These profiles provide a new and non-invasive probe of human metabolism by demonstrating the relative predominance of synthesis versus clearance of a VOC in vivo.

These breath profiles were evaluated in clinical studies of patients with breast cancer, cardiac chest pain, and heart transplant rejection. The breath profiles of normal controls and-patients with and without disease were compared by logistic regression analysis.

The breath alkane profile was determined in 35 women undergoing screening mammography. 10 had biopsy-proven breast cancer. The breath alkane profiles identified the women with breast cancer with 100% sensitivity and specificity.

The breath alkane profile was determined in 8 patients with unstable angina pectoris and in 50 normal controls with no known history of heart disease. The breath alkane profiles identified the patients with unstable angina pectoris with 100% sensitivity and specificity. The changes in the breath alkane profile were exaggerated during subsequent coronary angioplastry.

The breath alkane profile was determined in 19 patients with acute onset chest pain in a hospital emergency department. Ten had unstable angina pectoris and nine had an acute myocardial infarction. Compared to 50 normal controls with no known history of heart disease, the breath alkane profiles identified the patients with cardiac chest pain, and distinguished unstable angina pectoris from acute myocardial infarction with 100% sensitivity and specificity.

The breath alkane profile and breath alkyl alcohol profile were determined in 213 studies of heart transplant recipients. Two pathologists reviewed the endomyocardial biopsies independently, and agreed that no treatment was required in 182, but treatment was required in 13. The combination of the breath alkane profile and the breath alkyl alcohol profile identified heart transplant rejection requiring treatment with 84.6 sensitivity and 80.2% specificity.

The advanced new breath test appears to provide a highly, sensitive and specific test for breast cancer, cardiac chest pain and heart transplant rejection. The profiles were different from one another in all conditions. The breath alkane profile was displaced downward in the patients with breast cancer, and upward in the patients with ischemic heart disease. Both the breath alkane profile and the alkyl alcohol profile were displaced upward in heart transplant rejection. These results of the breath tests are consistent with the documented pathophysiology of OFRs in these disorders.

BRIEF DESCRIPTION OF THE DRAWINGS AND TABLES

Figure 1:
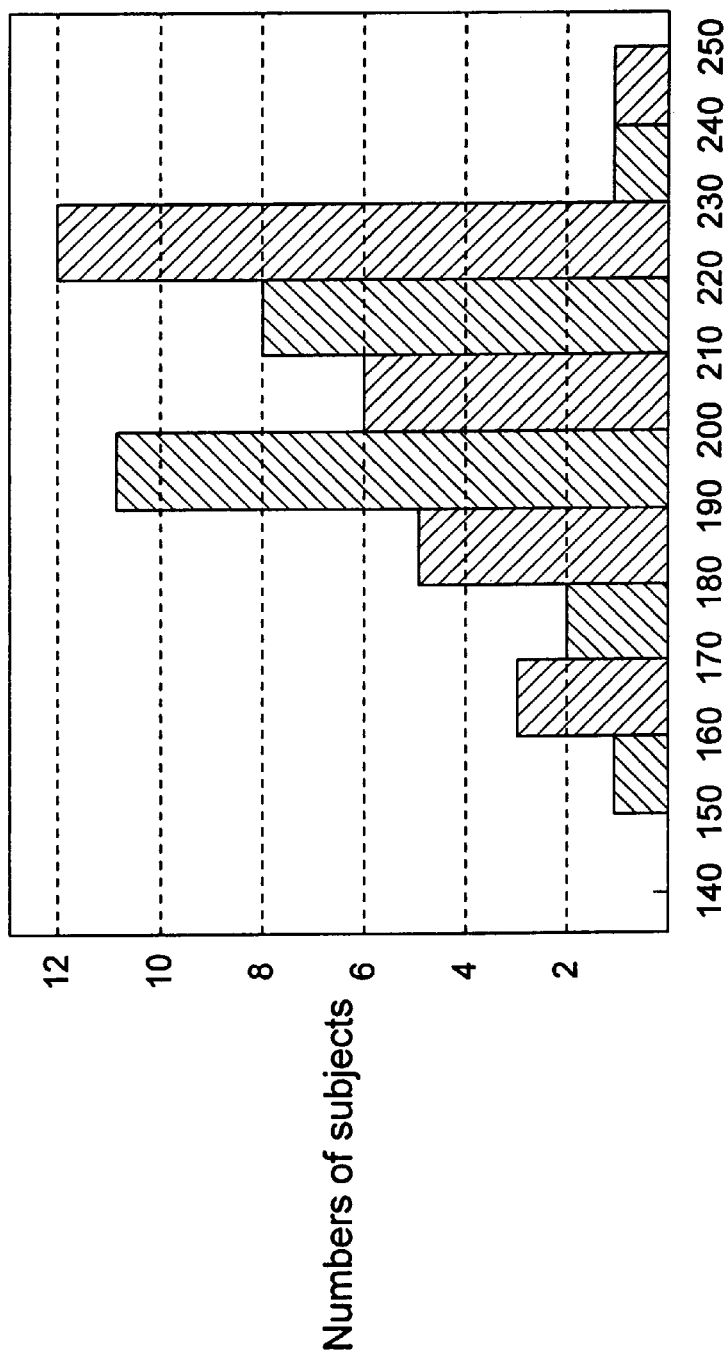

FIG. 1: (Prior Art) Inter-individual variation in number of VOCs in breath. Frequency distribution of number of VOCs observed in breath samples from normal humans.

Figure 2:
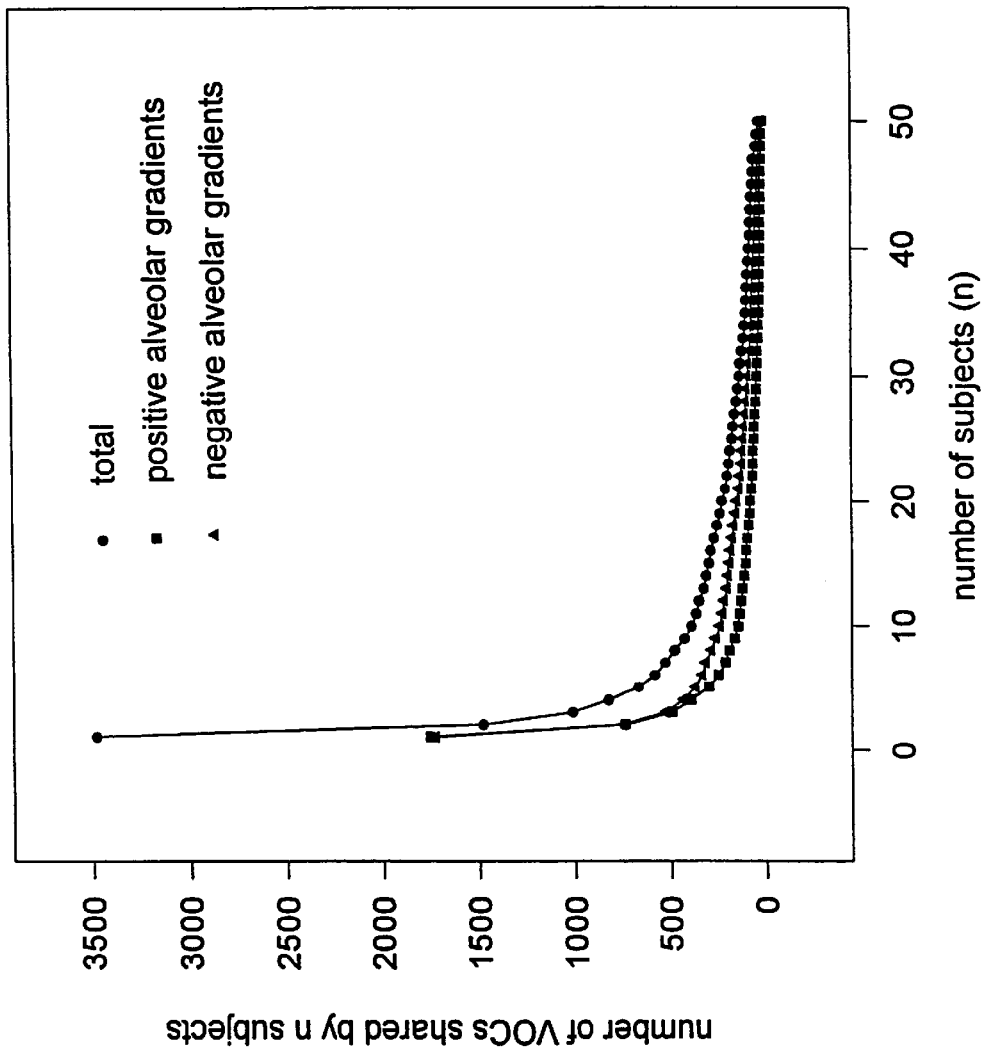

FIG. 2: (Prior Art) Variation in number of shared VOCs with sample size; 3481 different VOCs observed at least once, comprising 1753 VOCs with positive alveolar gradients and 1728 VOCs with negative alveolar gradients. Only 9 VOCs with positive alveolar gradients and 18 VOCs with negative alveolar gradients were observed in all 50 normal humans subjects.

Figure 3:
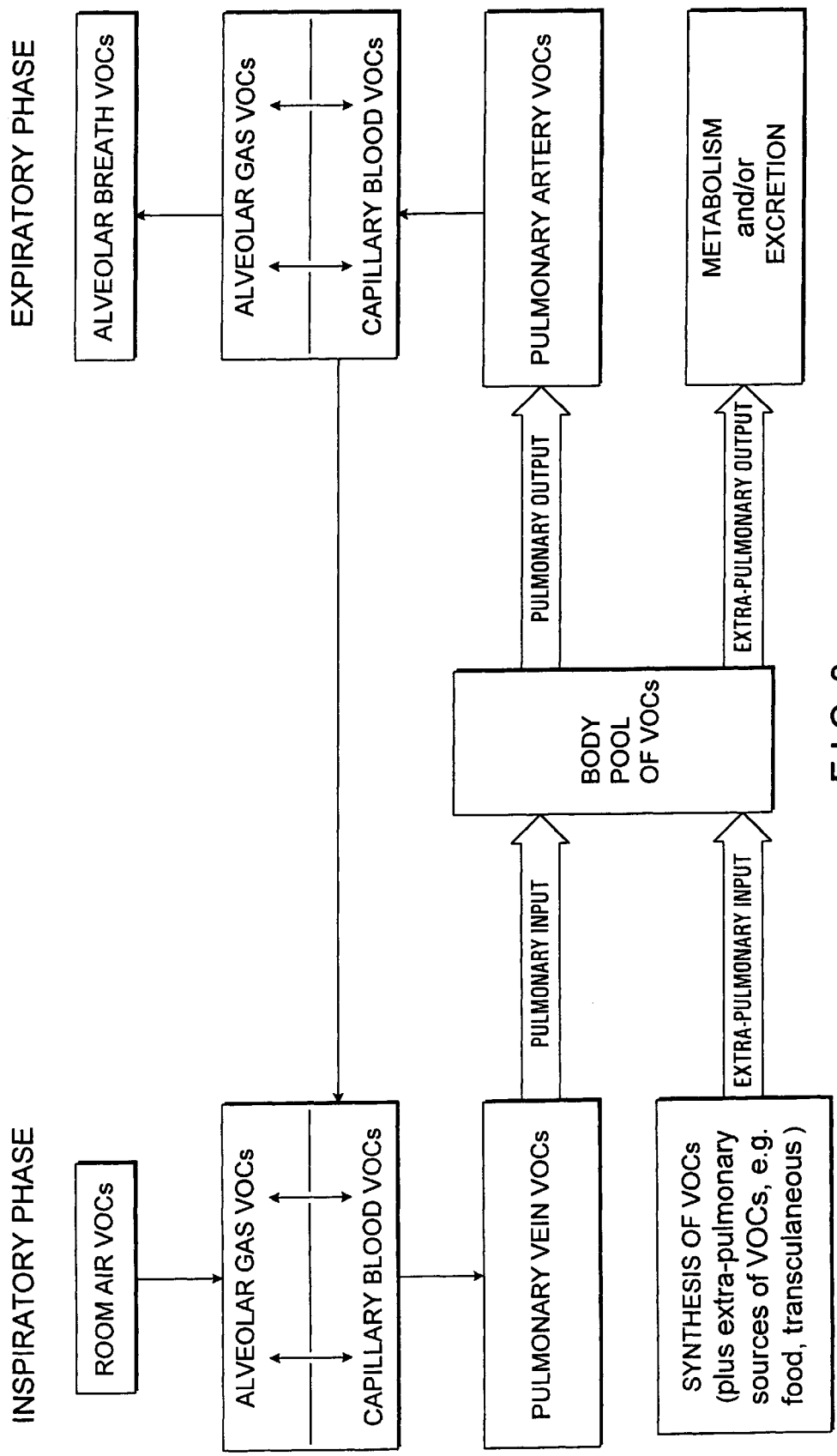

FIG. 3: (Prior Art) Pathways of VOCs through body compartments. Gaseous and capillary VOCs equilibrate rapidly in the pulmonary alveoli, and the dominant process varies with the phase of respiration. During the inspiratory phase, room air VOCs equilibrate with pulmonary venous blood, while during the expiratory phase, pulmonary arterial blood equilibrates with VOCs in alveolar breath. Extrapulmonary input of VOCs is primarily from endogenous synthesis, and extrapulmonary output of VOCs is predominantly by metabolism in the liver and excretion in the kidneys.

Figure 4:
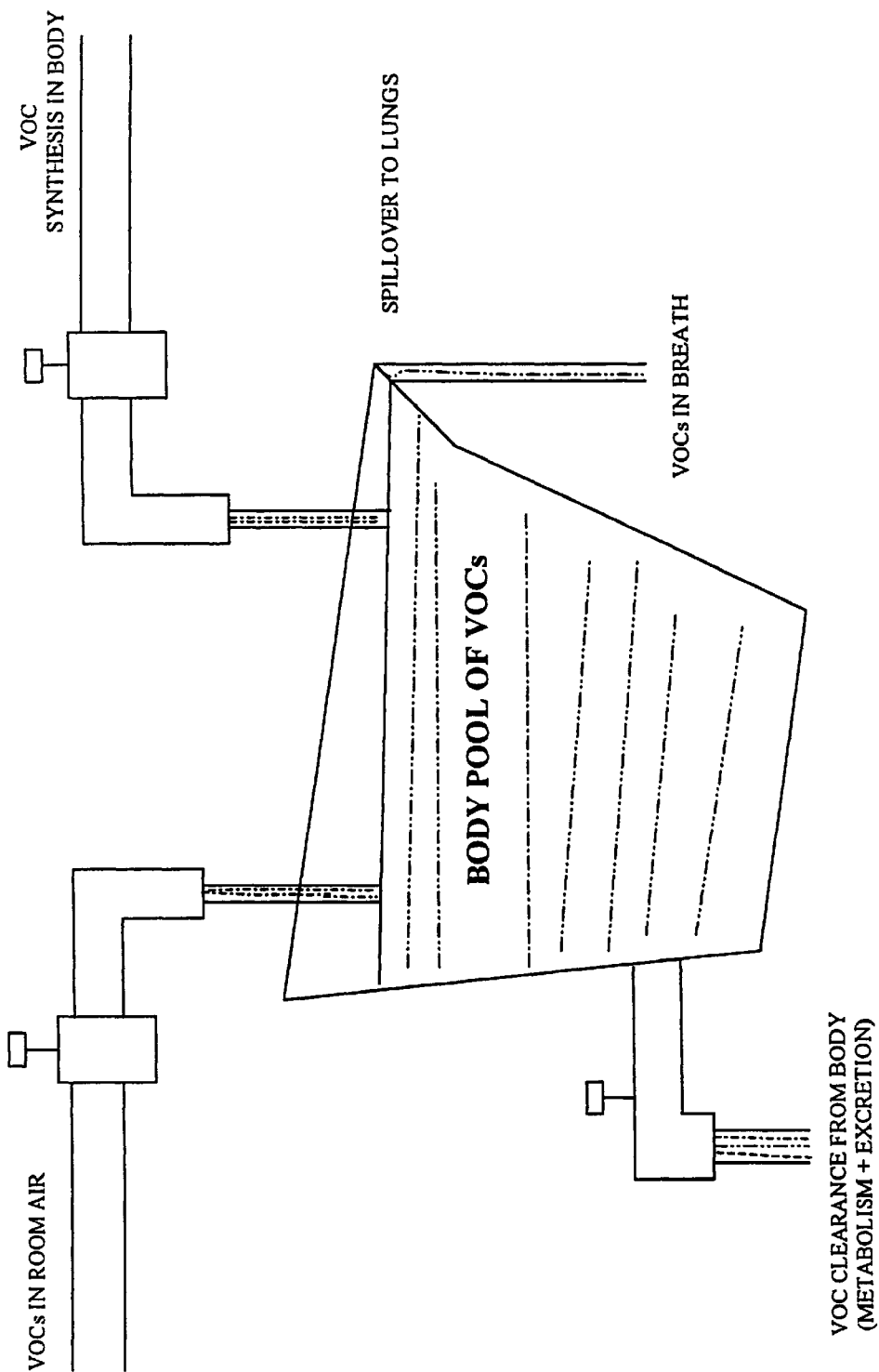

FIG. 4: (Prior Art) Water flow analogy of VOC kinetics: A VOC enters the body pool either from the inspired air or from synthesis in the body (ignoring minor inputs such as VOCs in foodstuffs). The VOC leaves the body pool either by clearance (metabolism and/or excretion) or else in the breath. If the VOC is neither synthesized nor cleared from the body, then the amount leaving in the breath must equal the amount entering from inspired air, and the alveolar gradient (amount in breath minus amount in air) will be zero. If the VOC is synthesized in the body but not cleared, more leaves in the breath than is inspired from the air, and the alveolar gradient becomes positive. Conversely, if the VOC is cleared from the body but not synthesized, less leaves in the breath than is inspired from the air, and the alveolar gradient becomes negative. Hence, if a VOC is both synthesized and cleared in the body, the polarity of the alveolar gradient will vary with their combined effect: positive if synthesis is greater than clearance, and negative if clearance is greater than synthesis.

FIG. 5: (Prior Art) Metabolism of alkanes. Polyunsaturated fatty acids in cell membranes are degraded to alkanes by lipid peroxidation mediated by oxygen free radicals, resulting in membrane dysfunction which may progress to cell death. The volatile alkanes are excreted in the breath, but may undergo further metabolism to alkyl alcohols. Potential metabolic pathways to other degradation products and to methylalkanes are speculative.

Figure 6:
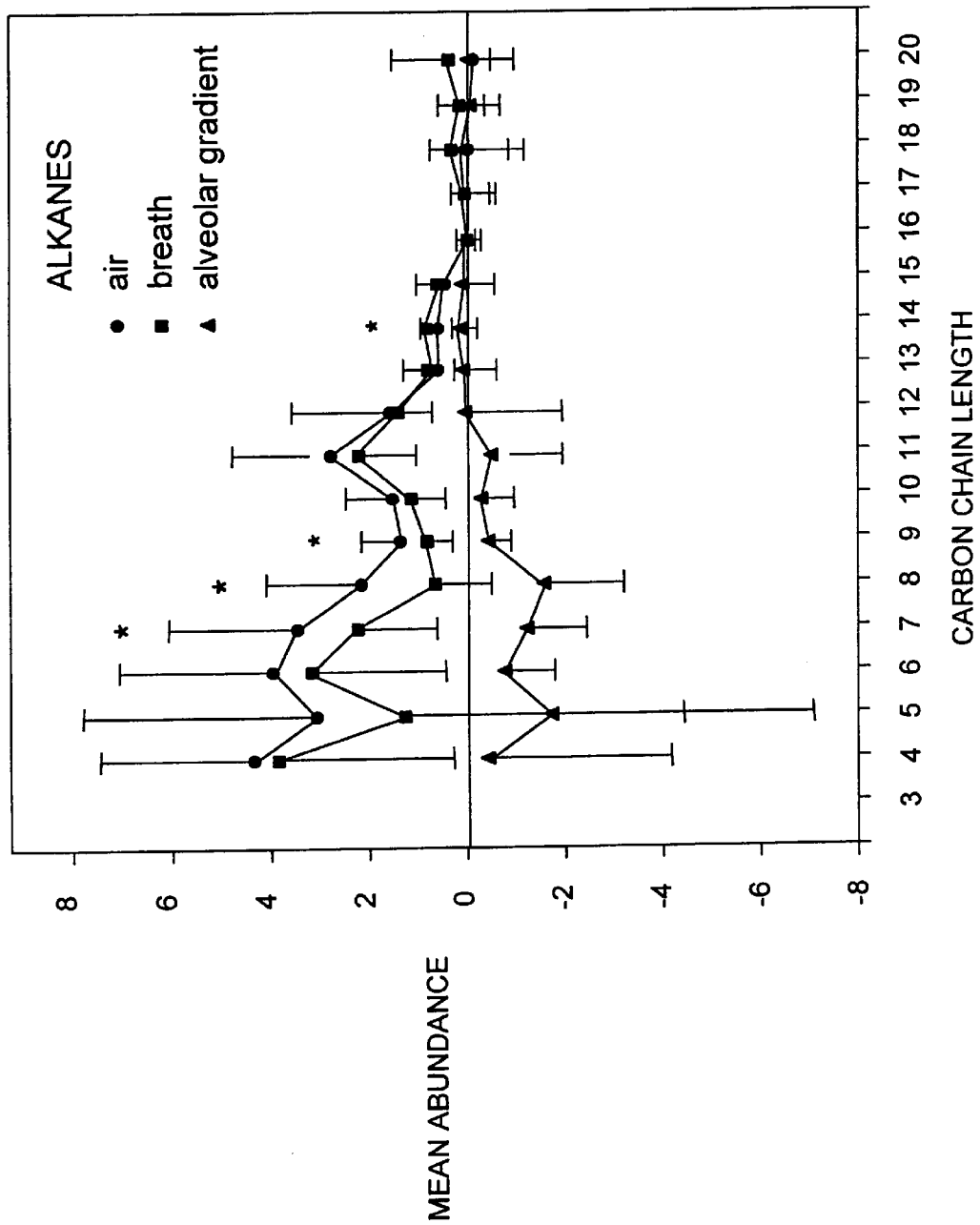

FIG. 6: (Prior Art) Alkanes in breath and air (normal healthy humans). The panel graph shows the abundance of alkanes in breath and air, the alveolar gradients, and their variation with carbon chain length.

Figure 7:
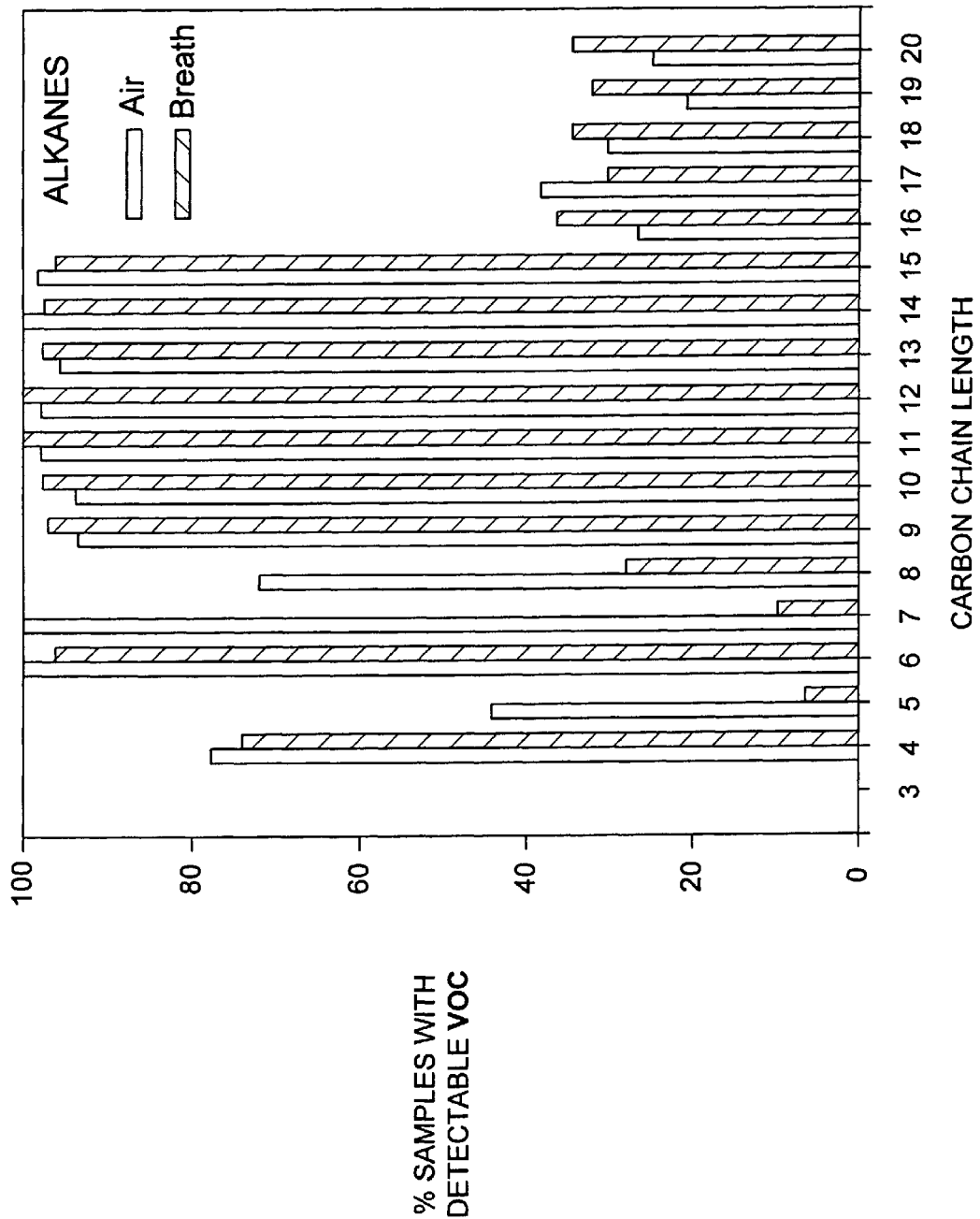

FIG. 7: (Prior Art) The panel shows the frequency distribution of the presence of alkanes in samples of breath and air (normal healthy humans).

Figure 8:
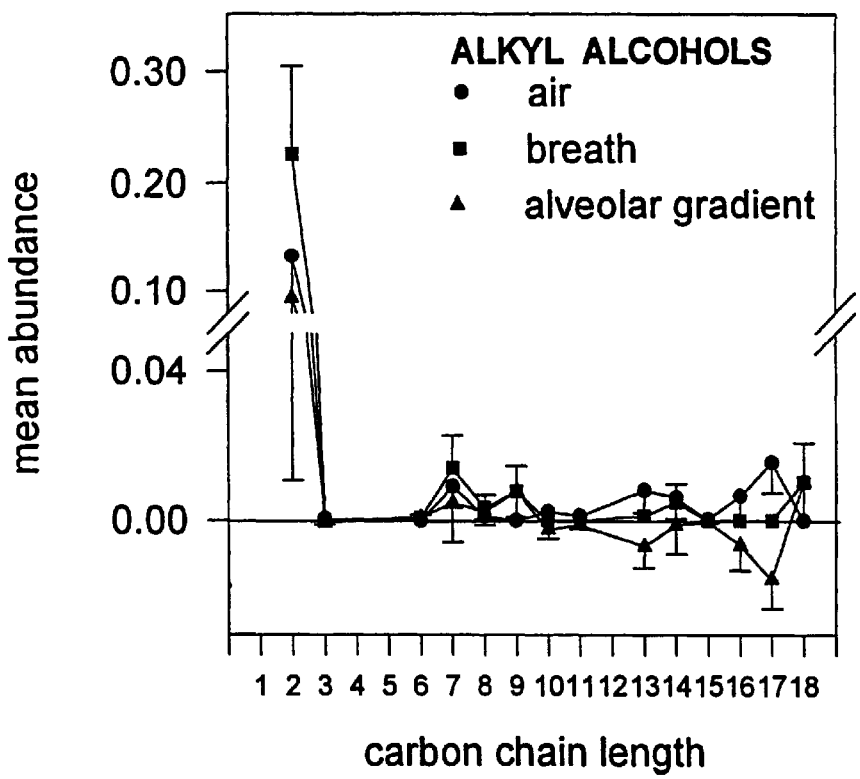

FIG. 8: (Prior Art) Alkyl alcohols in breath and air. The panel shows the abundance of alkyl alcohols in breath and air, the alveolar gradients, and their variation with carbon chain length (normal healthy humans).

Figure 9:
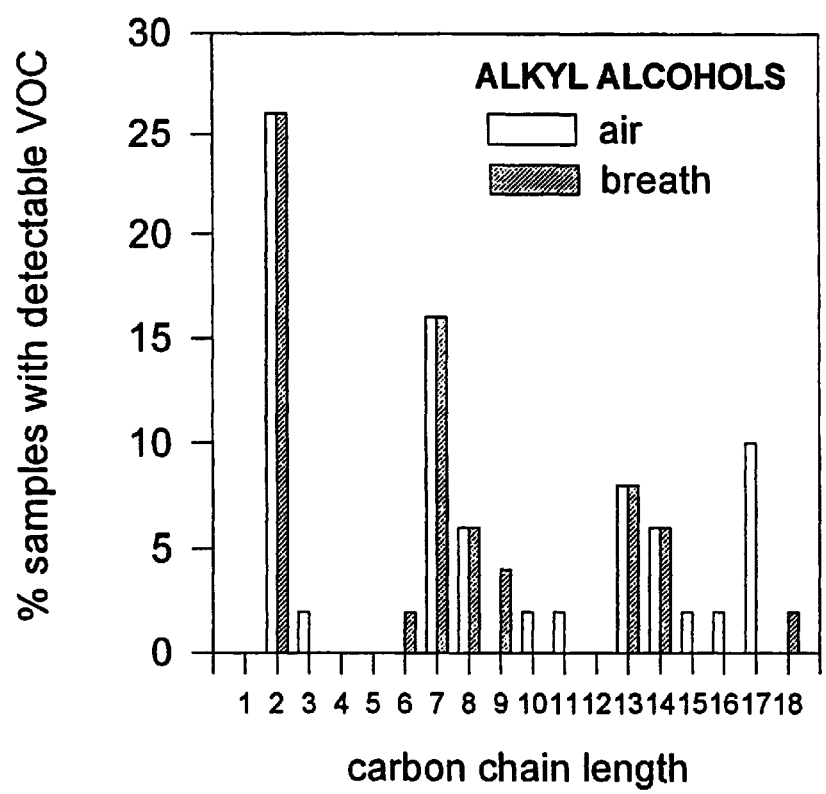

FIG. 9: (Prior Art) The panel shows the frequency distribution of the presence of alkyl alcohols in samples of breath and air (normal healthy humans).

Figure 10:
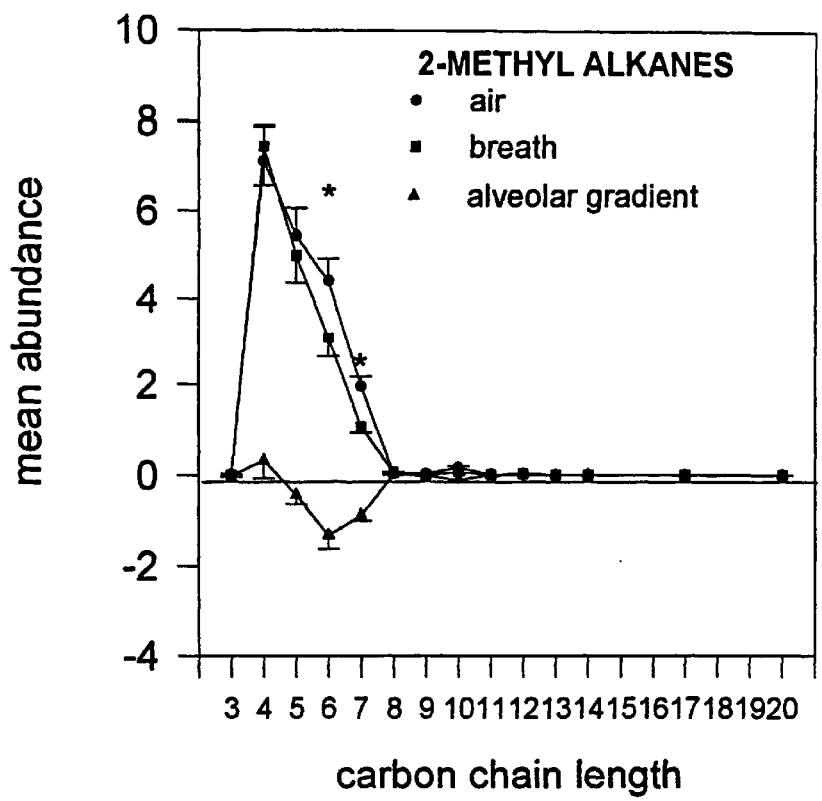

FIG. 10: (Prior Art) Methylalkanes in breath and air. The panel shows the abundance of methylalkanes in breath and air, the alveolar gradients, and their variation with carbon chain length (normal healthy humans).

Figure 11:
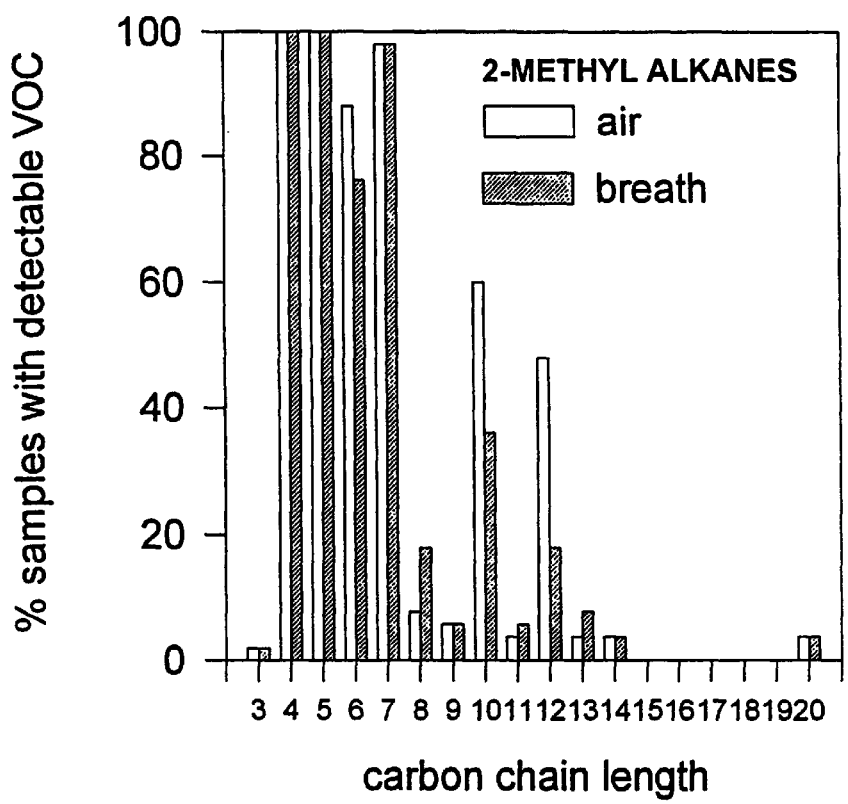

FIG. 11: (Prior Art) The panel shows the frequency distribution of the presence of methyl-alkanes in samples of breath and air.

Figure 12:
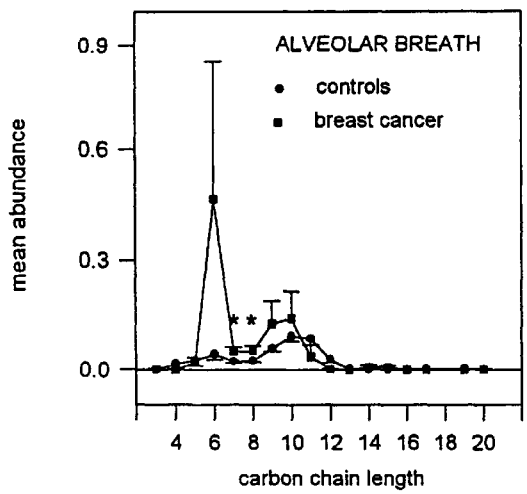

FIG. 12: shows graphically women with breast cancer and cancer-free controls: Alkane profile of alveolar breath.

Figure 13:
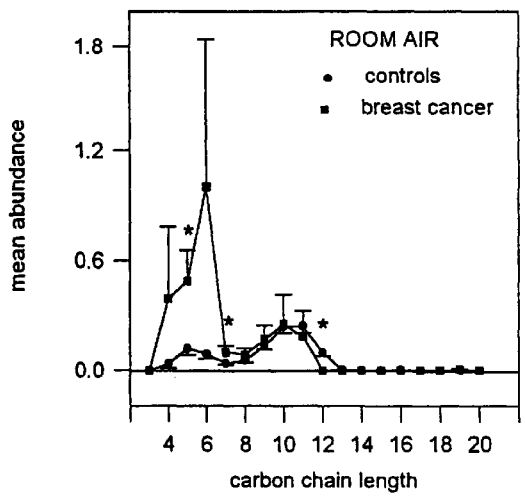

FIG. 13: shows graphically women with breast cancer and cancer-free controls: Alkane profile of room air.

Figure 14:
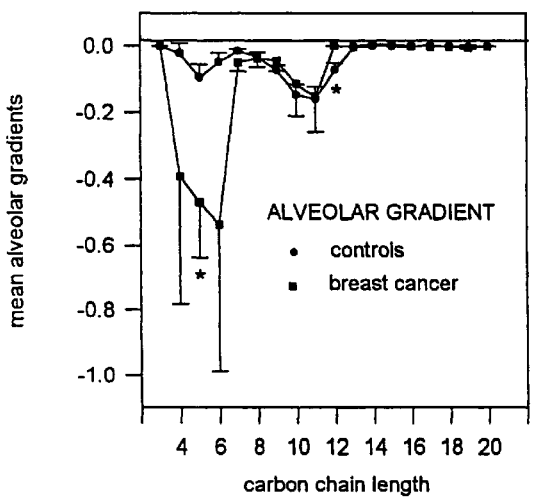

FIG. 14: shows graphically women with breast cancer and cancer-free controls: Alkane profile of alveolar gradient. The alkane profile was displaced downward in the women with breast cancer, compared to the cancer-free controls.

Figure 15:
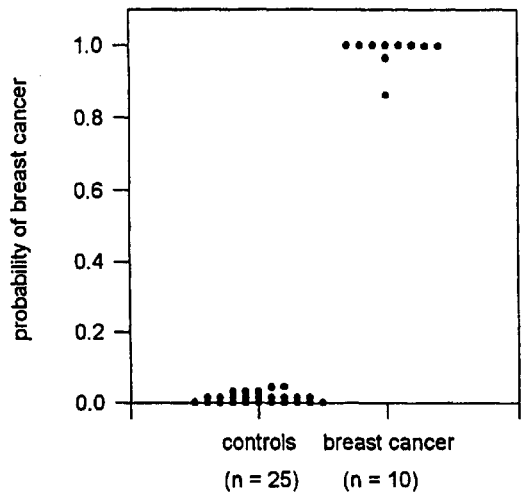

FIG. 15: shows graphically women with breast cancer and cancer-free controls: probability of breast cancer. The data shown in FIG. 14 was analyzed by logistic regression.

Figure 16:
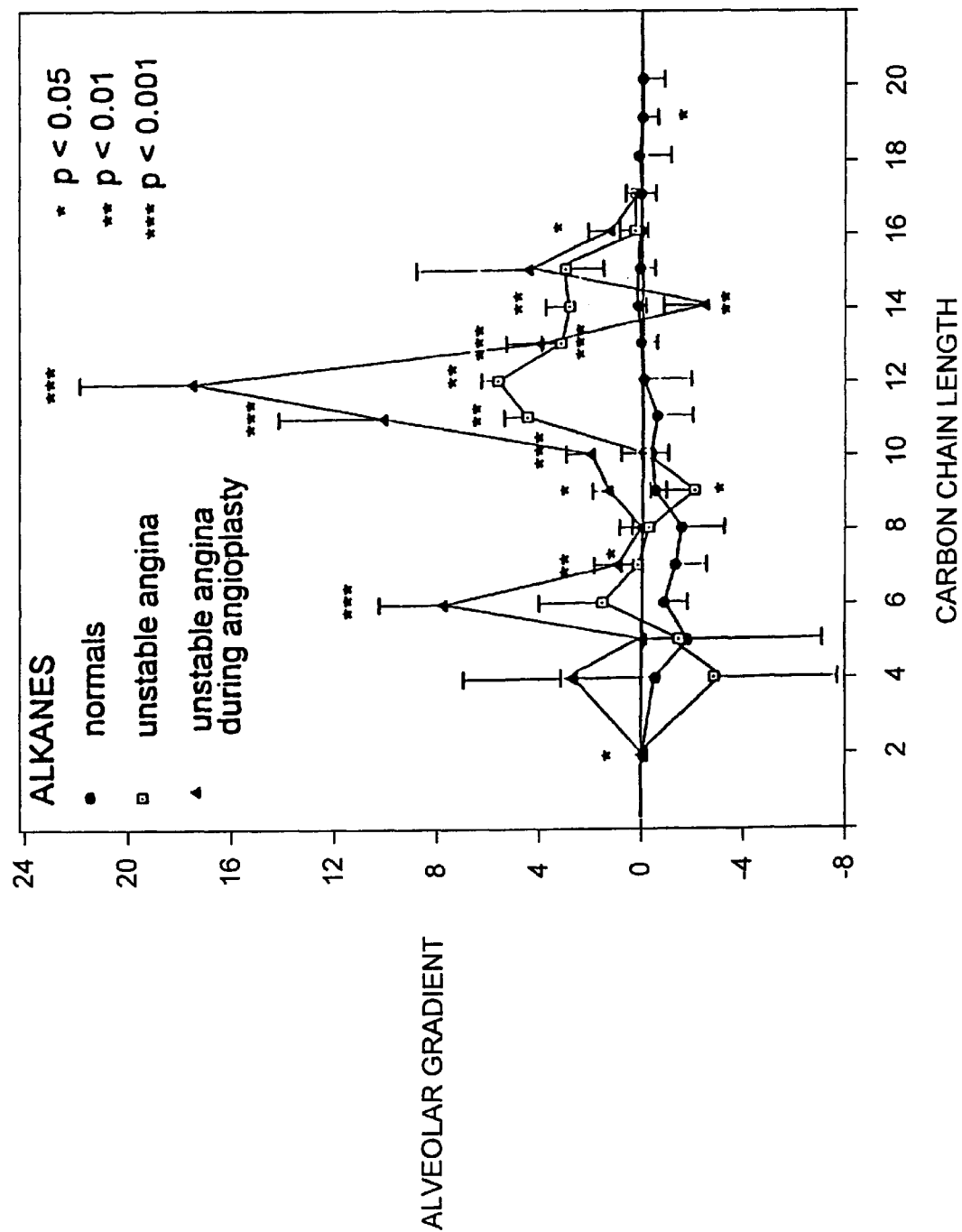

FIG. 16: Breath alkane profiles in normal controls and patients with unstable angina before and during coronary angioplasty: Compared to the normal controls, the breath alkane profile was displaced upwards in the patients with unstable angina. The breath alkane profile was displaced even further upwards during coronary angioplasty while the balloon was inflated.

Figure 17:
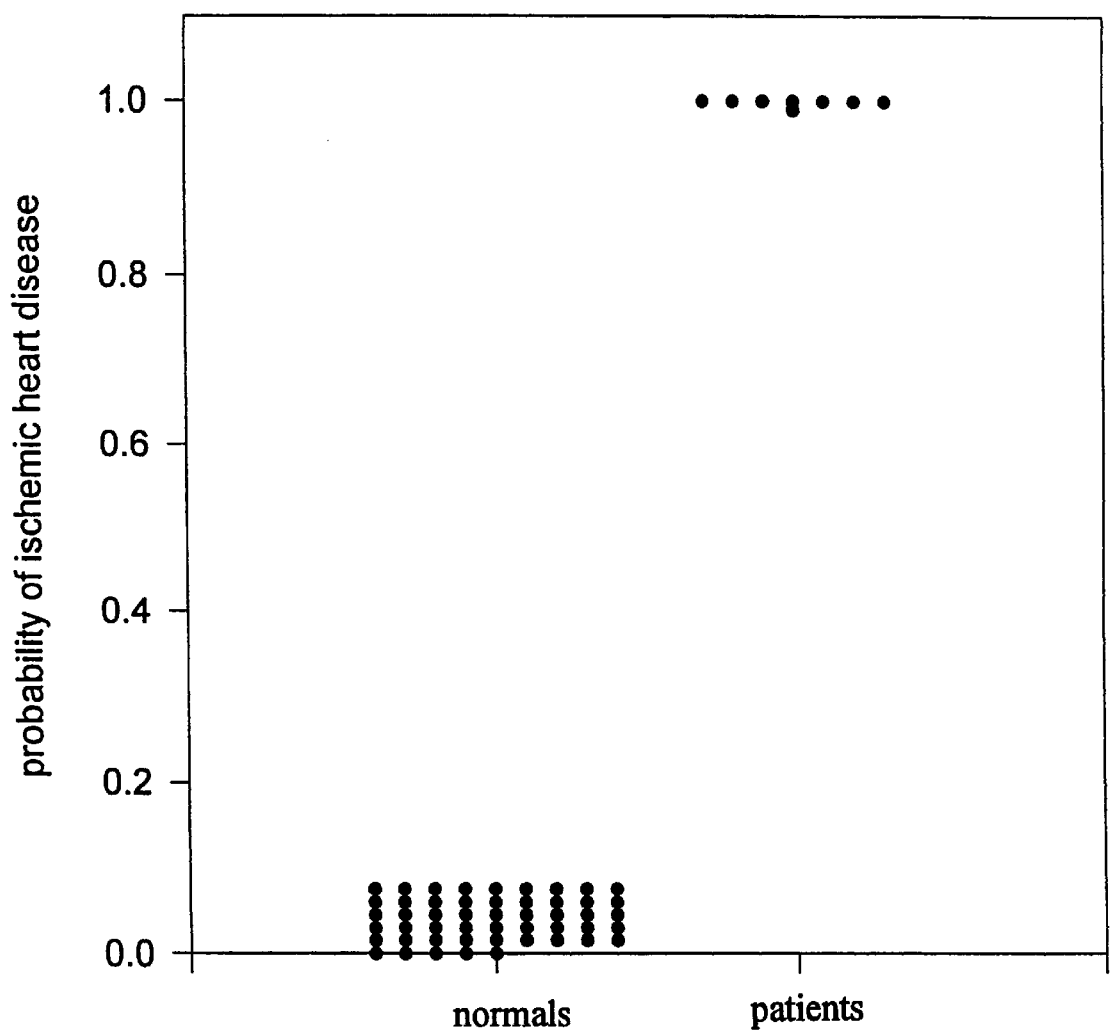

FIG. 17: Probability of ischemic heart disease in normal controls and patients with unstable angina: The data shown in FIG. 16 was analyzed by logistic regression, comparing the normal controls to the patients with unstable angina before they underwent coronary angioplasty. The probability was determined for each subject whether their breath alkane profile belonged to the normal group or to the unstable angina group. The classification accuracy was 100% for both groups.

Figure 18:
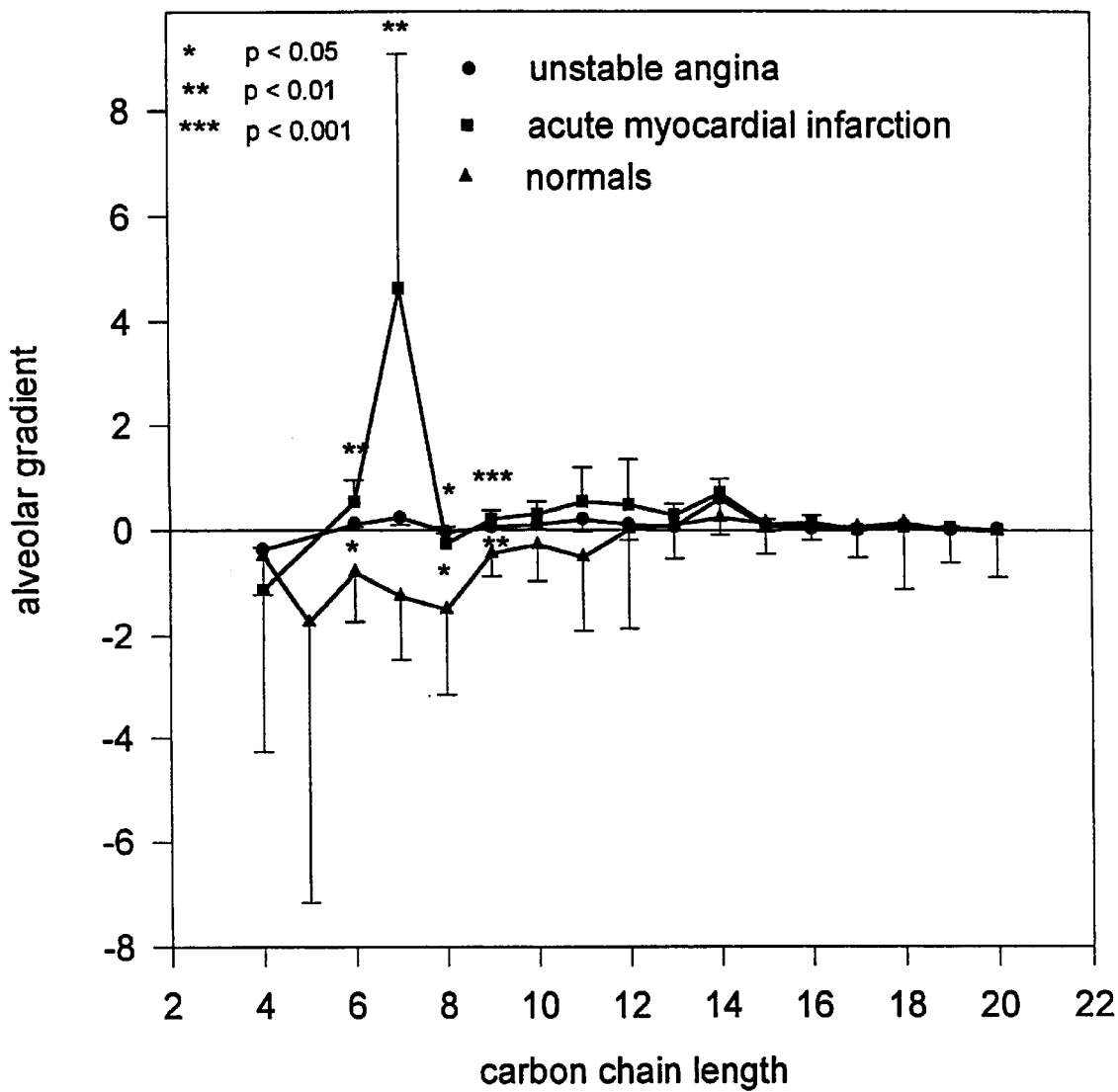

FIG. 18: Breath alkane profiles in normal controls and patients with chest pain due to unstable angina and acute myocardial infarction: Compared to the normal controls, the breath alkane profile was displaced upwards in the patients with unstable angina. The breath alkane profile was displaced even further upwards in the patients with acute myocardial infarction.

Figure 19:
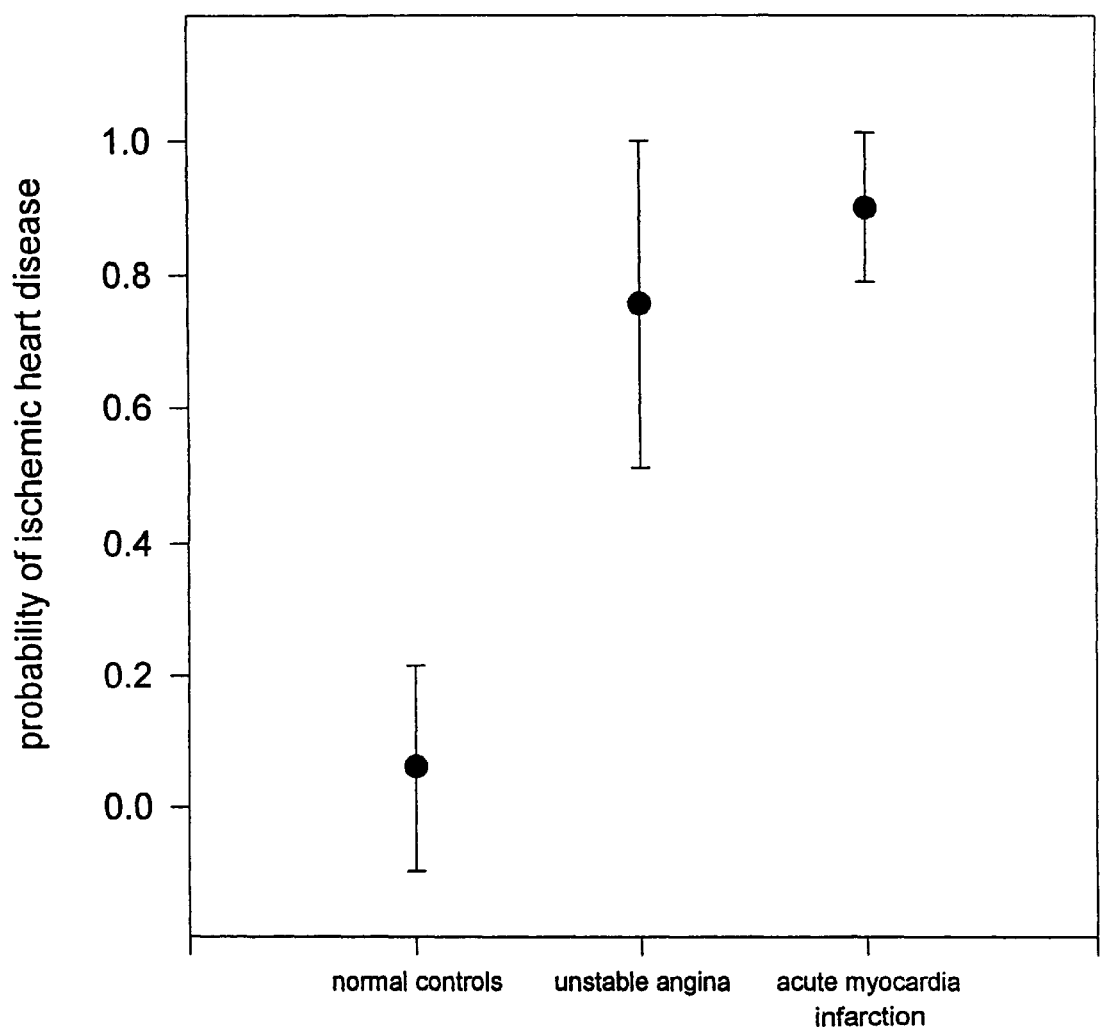

FIG. 19: Probability of ischemic heart disease in normal controls and patients with chest pain due to unstable angina and acute myocardial infarction: The data shown in FIG. 18 was analyzed by logistic regression, comparing the normal controls to the patients with cardiac chest pain. The probability was determined for each subject whether their breath alkane profile belonged to the normal group or to the cardiac chest pain groups (i.e., those with unstable angina or acute myocardial infarction). The classification accuracy was 100% for all groups.

Figure 20:
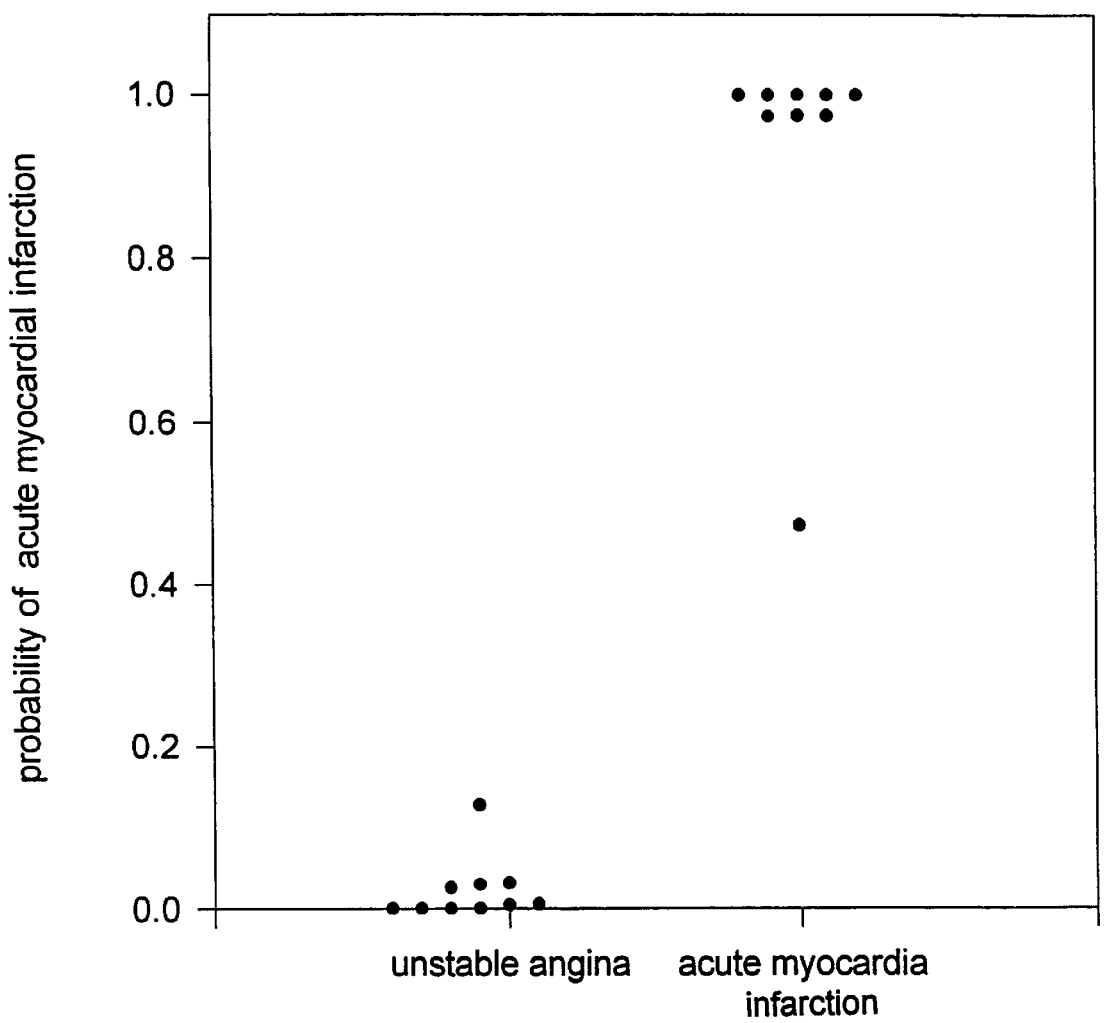

FIG. 20: Probability of acute myocardial infarction in patients with chest pain due to unstable angina and acute myocardial infarction: The data shown in FIG. 18 was analyzed by logistic regression, comparing the two groups of patients with cardiac chest pain. The probability was determined for each subject whether their breath alkane profile belonged to the unstable angina group or the acute myocardial infarction group. The classification accuracy was 100% for both groups.

Figure 21:
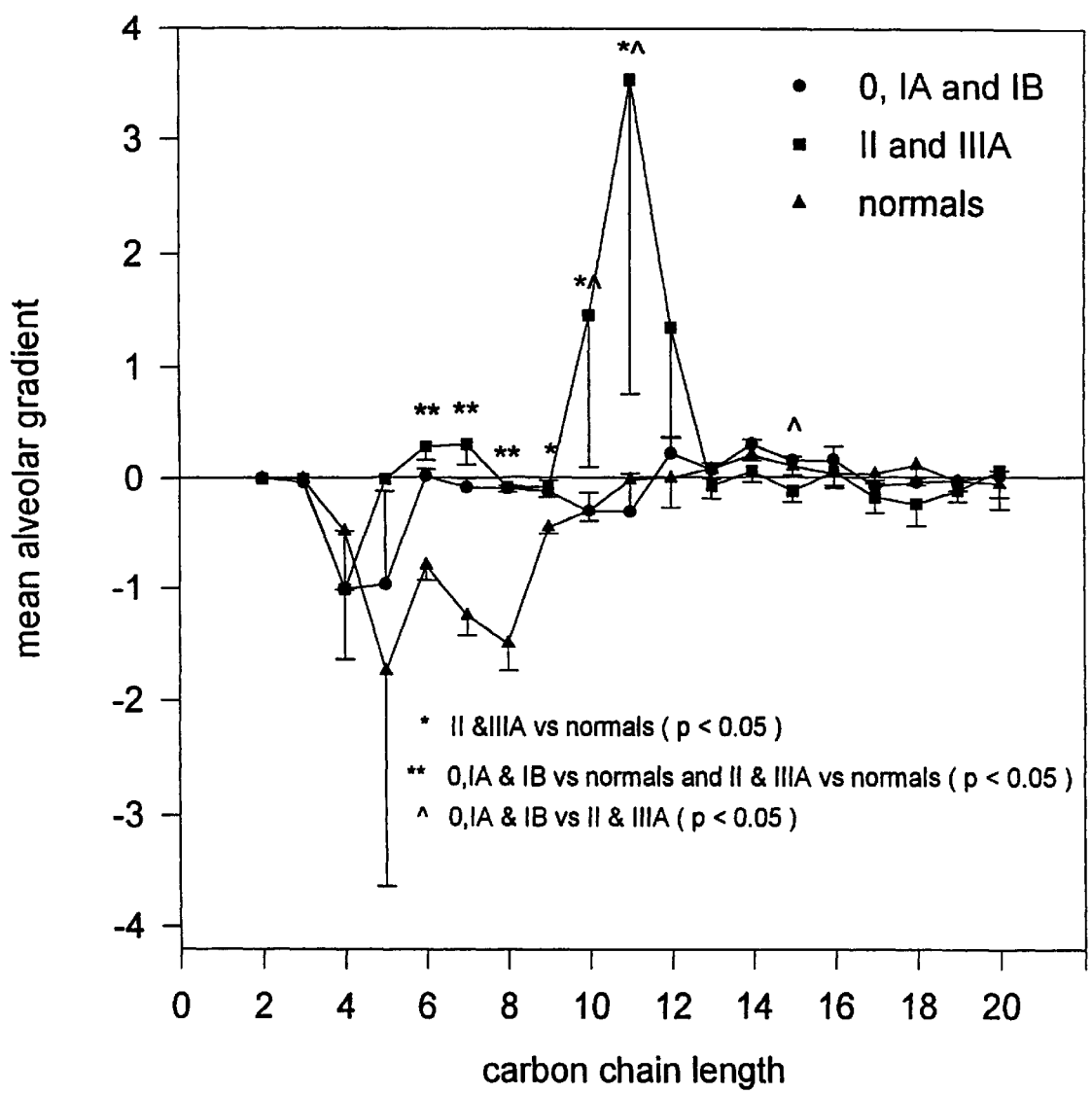

FIG. 21: Breath alkane profiles in normals and heart transplant recipients. Patients with heart transplants were divided into two groups: those requiring no treatment (endomyocardial biopsy with rejection grades 0, 1a and 1b) and those requiring treatment (endomyocardial biopsy with rejection grades II and III). Compared to the normal controls, the breath alkane profile was displaced upwards in the heart transplant recipients requiring no treatment, and an even further upwards in the heart transplant recipients requiring treatment.

Figure 22:
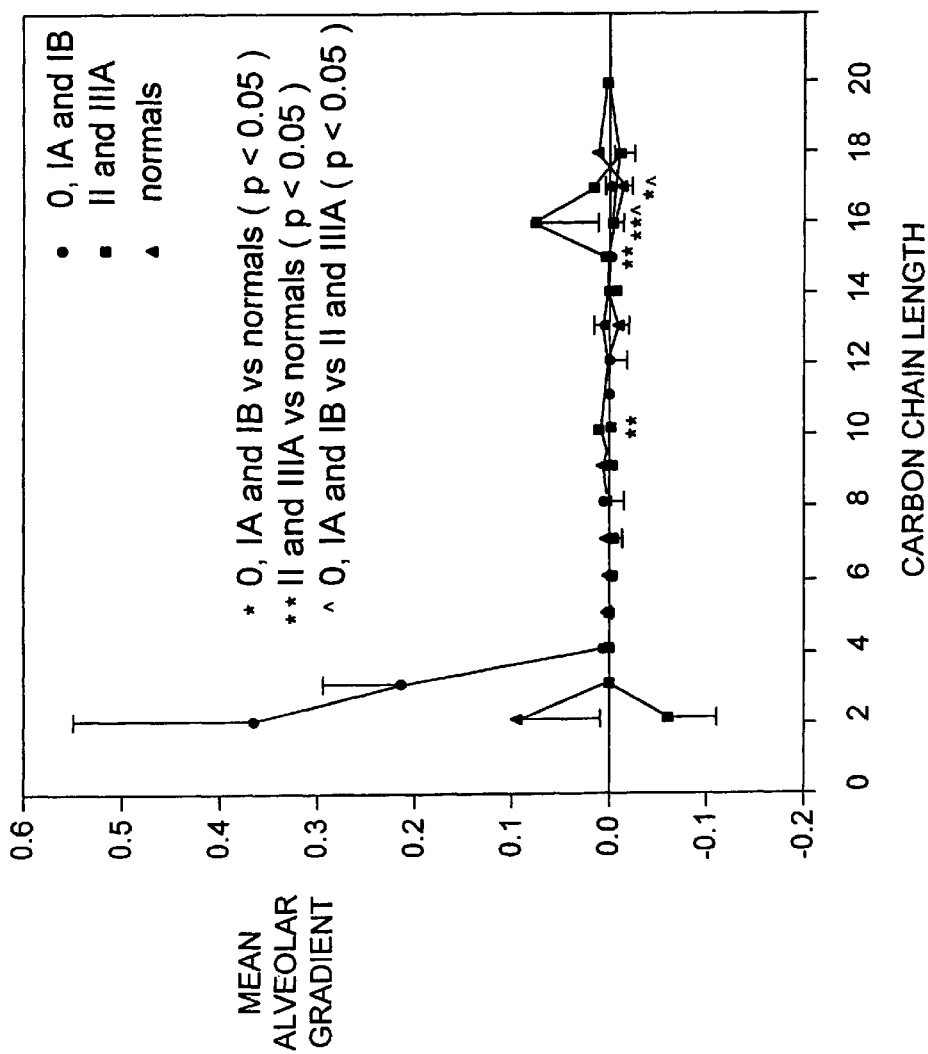

FIG. 22: Breath alkyl alcohol profiles in normals and heart transplant recipients. Patients with heart transplants were divided into two groups: those requiring no treatment (endomyocardial biopsy with rejection grades 0, 1a and 1b) and those requiring treatment (endomyocardial biopsy with rejection grades II and III). Compared to the normal controls, the breath alkyl alcohol profile was displaced upwards in the heart transplant recipients requiring no treatment, and even further upwards in the heart transplant recipients requiring treatment.

Figure 23:
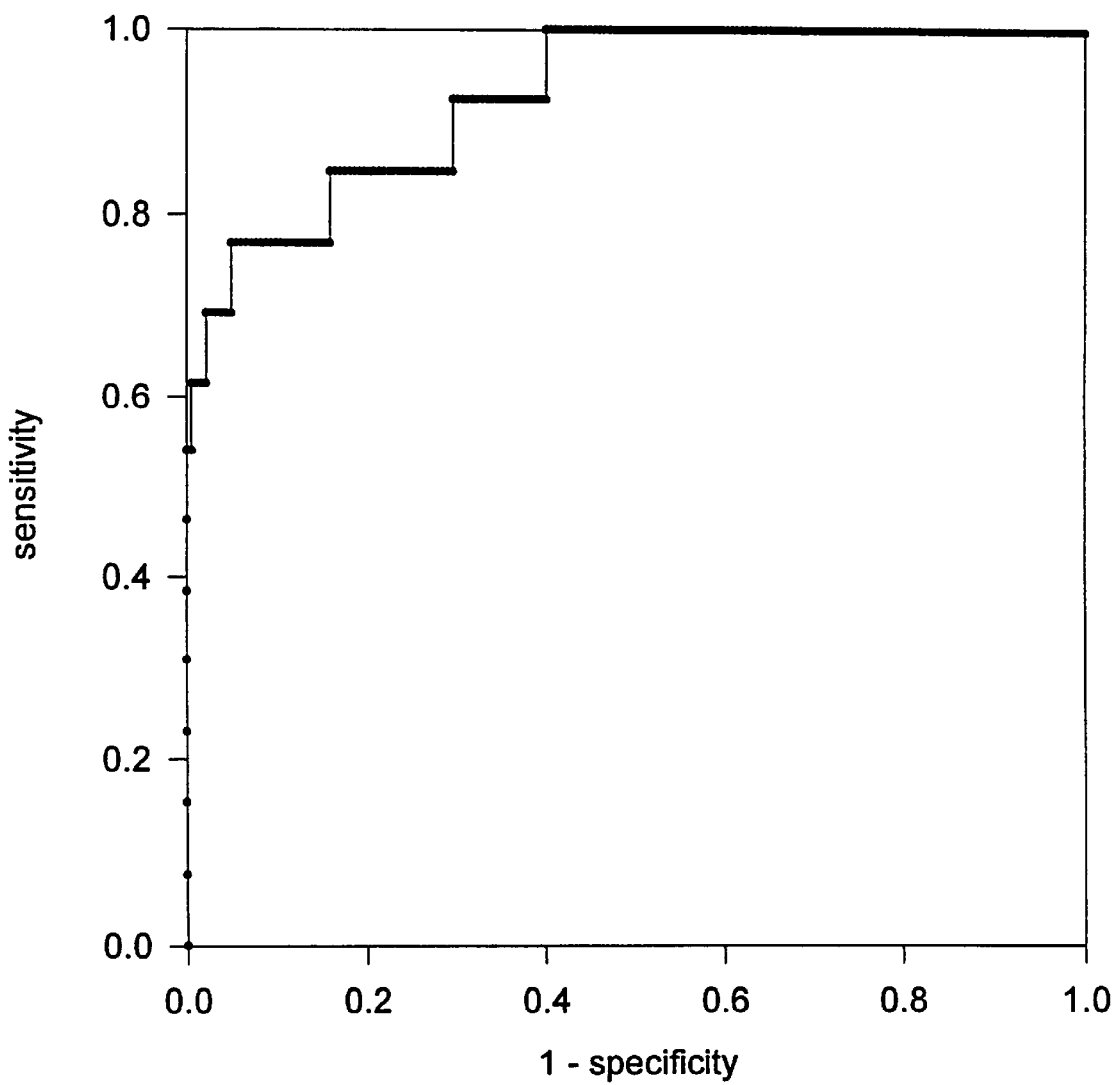

FIG. 23: Receiver operating characteristic (ROC) curve of the breath test for heart transplant rejection. Patients with heart transplants were divided into two groups: those requiring no treatment (endomyocardial biopsy with rejection grades 0, 1a and 1b) (n=182) and those requiring treatment (endomyocardial biopsy with rejection grades II and III) (n=13). The two groups were compared by logistic regression, employing the combination of the breath alkane profiles and breath alkyl alcohol profiles shown in FIGS. 21 and 22. The ROC curve displays the sensitivity and specificity of the test. At the shoulder of the curve, the breath test was 84.6% sensitive and 80.2% specific.

DETAILED DESCRIPTION OF THE PREFERRED EMBODIMENTS OF THE INVENTION

As described above, the methods of collecting and analyzing alveolar breath are well-known to those skilled in the art. The present invention comprises interpretation of the analytical results and profiling them to determine the presence or absence of disease in a human.

The term "alkane" or "n-alkane" as used herein means a hydrocarbon of the formula

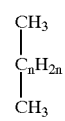

wherein n is an integer of 1 to 18.

The following examples demonstrate the manner and process for carrying out the invention and set forth the best mode contemplated by the inventor for practice of the invention.

The Apparatus for Breath VOC Collection and Analysis

The breath collection apparatus (BCA): This device has been described (Phillips, supra.). In summary, the BCA is a portable, microprocessor-controlled device with a heated breath reservoir which prevents condensation of water. Alveolar breath is pumped from the breath reservoir through a sorbent tube which captures the VOCs on activated carbon. In this study, modified sorbent tubes were employed containing 200 mg Carbotrap C (20/40 mesh) and 200 mg Carbopack B (60/80 mesh) (Supelco, Inc, Bellefonte, Pa.). The volume of the breath sample can be varied via a panel-mounted timer and flow meter, and the geometry of the system ensures that the sample comprises alveolar breath virtually uncontaminated by dead-space air.

Collection of a Breath Sample:

Subjects breathed into the BCA through a disposable mouthpiece. The BCA presented minimal resistance to expiration because the wide-bore breath reservoir (1.0 inch dia) was open to the air at its far end. Samples could be collected even from elderly or bedridden patients without causing discomfort. The collection period was 2.0 min at 0.5 1/min, and two samples were collected: one of breath, and one of background room air.

Assay Instrumentation and Procedure:

VOCs were desorbed from the sorbent tubes and concentrated in an automated thermal desorber (ATD 400, Perkin Elmer, Norwalk, Conn.), separated in a gas chromatoraph, and identified and quantitated in a mass spectrometer (HP6890 and mass selective detector 5973, Hewlett Packard, Palo Alto, Calif.). Sorbent tubes were loaded onto a carousel (capacity 50), checked for leaks, then purged with helium for 1.0 min to remove water vapor and air. An internal standard (0.25 ml 2 ppm 1-bromo-4-fluorobenzene, Supelco Inc, Bellefonte, Pa.) was added via the ATD 400 standard injection accessory. The sample was desorbed at 300° C. onto a 0° C. cold trap (low flow ATD 400 air monitoring trap) for 4 min (helium flow 50 ml/min, outsplit flow 2.0 ml/min). The cold trap was then heated rapidly to 300° C. and the desorbed sample was flushed through a fused silica transfer line (0.25 m.m. ID, 200° C. helium flow 1.25 ml/min) to the chromatography column (SPB-5 capillary column, 30 m×0.25 m.m.×0.25 um film thickness, Supelco Inc, Bellefonte, Pa.). Column temperatures were ramped as follows: 0° C. for 8 min, 4° C./min to 138° C., 0.10 min hold, 10° C./min to 210° C. 0.10 min hold, and 30° C./min to 300° C., 0.25 min hold.

Data Management:

Data from each chromatographic peak, comprising retention time, chemical identity (as identified by Wiley 138 library), area under curve (AUC), and quality of fit, were automatically downloaded into a spreadsheet (Excel 4.0, Microsoft, Redmond, Wash.) and consolidated in a relational database (Paradox, Borland, Scotts Valley, Calif.). The alveolar gradient of each VOC was calculated as:

$$(AUC_{VOC\ in\ breath} - AUC_{VOC\ in\ air})/AUC_{internal\ standard}$$

The Kinetic Determinants of the Alveolar Gradient

FIG. 3 demonstrates the pathways which VOCs follow through different compartments of the body. Equilibration is rapid in the pulmonary alveoli, so that the concentration of a VOC in alveolar breath is determined by its concentration in pulmonary arterial blood, while the concentration of a VOC in room air determines its concentration in pulmonary venous blood. The body pool of VOCs is derived from two sources: pulmonary input (from room air) and extrapulmonary input (principally from synthesis in the body, although exogenous sources of VOCs such as foods, drugs, and percutaneous absorption may also contribute). VOCs leave the body pool by two routes: either by pulmonary output (in alveolar breath) or by extrapulmonary output (clearance by metabolism and/or excretion). The kinetics of a VOC in the body may also be modeled by the flow of water into and out of a common pool (FIG. 4).

Kinetic analysis demonstrates that the alveolar gradient of a VOC varies with the rate of synthesis of the VOC minus its rate of clearance from the body (see Appendix 1: Kinetic analysis of the determinants of the alveolar gradient). The polarity of the alveolar gradient indicates which of the two processes is predominant. If the alveolar gradient is positive, the rate of synthesis is greater than the rate of clearance; conversely, if the alveolar gradient is negative, then the rate of clearance is greater than the rate of synthesis. As an example, the mean alveolar gradient of the long-chain n-alkane tetradecane was positive, demonstrating that in vivo synthesis predominated over clearance. Conversely, the mean alveolar gradient of methylbenzene was negative, demonstrating that clearance was greater than in vivo synthesis. This was consistent with ingestion of methlybenzene as a pollutant of room air which was then cleared from the body by metabolism and excretion.

The Composition of Breath VOCs in Normal Humans

Despite numerous studies of pentane and several other breath VOCs, the range of composition of VOCs in normal human breath has not been well defined. Early studies reported substantial quantitative and qualitative differences amongst small groups of normal humans: concentrations of breath VOCs varied widely, and a number of VOCs were detectable in the breath of some subjects but not in others (Conkle J P, Camp B J and Welch B E: Trace composition of human respiratory gas, Arch Environ Health 1975; 30:290–295);

Barkley J. Bunch J. Bursey J T et al: Gas chromatography mass spectroscopy computer analysis of volatile halogenated hydrocarbons in man and his environment—a multimedia environmental study, Biomedical Mass Spectrometry 1980; 7(4): 139)–147). The composition of breath VOCs was investigated in normal humans (Example 1).

Human Subjects:

50 normal human subjects were studied employing the method described above. They comprised 27 males (mean age 38.8 yr, SD=12.8) and 23 females (mean age 38.65 yr, SD=11.4).

Inter-individual Variation in Number of VOCs:

The number of VOCs detected in each breath sample ranged from 157 to 241 (mean=204.2, SD=19.8, CV=9.7%) (FIG. 1). 3481 different VOCs were observed at least once, 1753 with positive alveolar gradients and 1728 with negative alveolar gradients, but the majority of these were observed in only one subject. Only 27 VOCs were observed in all subjects (FIG. 2).

Inter-individual Variation in Frequency and Abundance of COCs:

VOCs were ranked by the frequency with which they were observed in different subjects (Table 1, below) and by their relative abundance in the breath (Table 2, below).

Discussion:

More than 200 different VOCs were observed in most breath samples, and more than 3000 different VOCs were observed at least once. These numbers probably represent an underestimate of the total number of VOCs in normal human breath, since the assay was limited to C3 to C20 VOCs within the trapping range of the sorbent traps. The majority of these VOCs were observed only once. The number of breath VOCs observed in more than one subject fell rapidly as the size of the group increased, and only a comparatively small number of commonly occurring VOCs were observed consistently in the majority of the population.

Several of the commonly occurring VOCs were derived from metabolic pathways that have been previously reported e.g. isoprene from the mevalonic acid pathway of cholesterol synthesis (Stone B G, Besse T J, Duane W C, Evans C D and DeMasster E G: Effect of regulating cholesterol biosynthesis on breath isoprene excretion in men; Lipids 1993; 28:705–708), acetone from glucose metabolism, (Stewart R D and Boettner E A: Expired-air acetone in diabetes mellitus; New England Journal of Medicine, 1964; 270:1035–1038), and alkanes from OFR-mediated lipid peroxidation of fatty acids. However, the source of commonly occurring VOCs such as napthalene and 1-methyl-napthalene is not yet known. They may be degradation products of steroids, but further studies are required to determine their origin.

The actual concentration of each VOC in molar or mass units was not determined because this would have required the construction of more than 3000 different standard curves, a very considerable undertaking. Instead, we determined the ratio of the area under curve (AUC) of the chromatographic peak of each WOC to the AUC of the internal standard. This value is a correlate of molar concentration, and it was used to estimate the abundance of each VOC in breath and air.

The relative abundance of each VOC was then ranked by its alveolar gradient i.e. abundance in breath minus abundance in room air.

The results of this study (Example 1) accorded with previous reports that normal humans differ widely from one another in the composition of their breath VOCS, both qualitatively and quantitatively. However, it also demonstrated two points of similarity between individuals which have not been previously reported: First, the total number of breath VOCs in each individual did not vary widely within a fairly narrow range. Second, despite the large total number of different VOCs observed, there was a comparatively small "common core" of breath VOCs which was present in all subjects, and which was probably produced by metabolic processes common to most humans.

The Breath Alkane Profile in Normal Humans

This Example 2 investigated the composition of alveolar breath in normal humans in order to determine the detectable spectrum of alkanes and alkane derivatives with different carbon chain lengths, the variation in the alveolar gradients of these VOCs, and the frequency of their occurrence in breath and in air.

MATERIALS AND METHODS

Breath collection apparatus (BCA) and assay: The method has been described in Example 1, supra.

Human Subjects:

Breath samples were collected from 50 normal volunteers comprising 27 males (mean age 38.8 yr, SD=12.8) and 23 females (mean age 38.65 yr, SD=11.4). All had fasted from the previous midnight and samples were collected between 7.00 am and 12.00 noon.

Analysis of Data:

The abundance of a VOC in breath or air was determined from the ratio $AUC_{VOC}/AUC_{internal\ standard}$ where AUC was the area under curve of the VOC peak on the chromatogram. The alveolar gradient was determined as:

$$(AUC_{VOC\ in\ breath} - AUC_{VOC\ in\ air})/AUC_{internal\ standard}.$$

RESULTS

The mean abundance of each VOC in breath and air, and its alveolar gradient are shown as these values varied with carbon chain length in alkanes (FIGS. 6–7), alkyl alcohols (FIGS. 8–9) and 2-methyl alkanes (FIGS. 10–11). The frequency with which each VOC was observed in samples of breath and air is also shown as a function of carbon chain length. Multiple t-tests revealed no significant differences between the alveolar gradients of alkanes, alkyl alcohols and 2-methyl alkanes in males and females.

Discussion:

n-alkanes ranging from C2 to C10 were detected in room air and in normal human breath. The absence of shorter or longer chain alkanes was probably due to the limited trapping range of the sorbent traps employed in this study. A distinctive and continuous profile of alveolar gradients was observed in alkanes of different chain lengths: mean values were negative from C4 to C11, and positive from C13 to C20 (FIGS. 6–7). These findings confirmed an earlier observation that the mean alveolar gradient of breath pentane was negative in normal humans (Phillips M. Sabas M. & Greenberg, J. supra.). The significance of this alveolar gradient profile may be inferred from analysis of VOC kinetics in the body:

$$\text{alveolar gradient} = C_{alveolar\ breath} - C_{room\ air}$$
$$= \frac{(R_{synthesis} - R_{clearance})}{RMV}$$

where R=rate of movement of VOC (mol/min), C=concentration of VOC (mol/l), and RMV=respiratory minute volume (l/min) (Appendix 1). Hence, these findings are consistent with the conclusion that in normal humans, the rate of clearance of alkanes was greater than the rate of synthesis for C4 to C12 alkanes, while the rate of synthesis was greater than the rate of clearance for C12 to C20 alkanes. The rate of synthesis of an alkane is principally determined by OFR-mediated lipid peroxidation of PUFAs, while the rate of clearance is most likely determined by degradation via the cytochrome P450 system;

(Crosbie S J, Blain P G and Williams F M: Metabolism of n-hexane by rat liver and extrahepatic tissues and the effect of cytochrome P-450 inducers (Hum Exp Toxicol 1997; 16(3):131–137;

Scheller U, Zimmer T. Kargel E and Schunck W H: Characterization of the n-alkane and fatty acid hydroxylating cytochrome P450 forms 52A3 and 52A4, Arch Biochem Biophys 1996; 328(2):245–54).

The frequency distribution of alkanes in breath and air (FIGS. 6–7) demonstrates that heptane was observed in all samples of room air but in 0% of alveolar breath samples. The most likely explanation is that inspired heptane was cleared from the body with high efficiency by metabolism and excretion, thereby reducing its concentration to undetectable levels in the pulmonary artery and the alveolar breath of 90% of the normal subjects. C5, C6, and C9 through C15 alkanes were present in nearly all samples of room air. These alkanes were probably derived from the breath of other humans. Further studies will be required to determine if this is a common characteristic of room air at other geographic sites. However, experience in our laboratory and elsewhere indicates that pentane can commonly be detected as a contaminant of room air when a sufficiently sensitive assay is employed (Cailleux A and Allain P: Is pentane a normal constituent of human breath? Free Radic Res Commun 1993; 18(6):323–7;

Phillips M. Sabas M. and Greenberg J: Alveolar gradient of pentane in normal human breath, Free Radical Research Communications 1994; 20(5):333–337).

Alkyl alcohols ranging from C2 to C18 were also detected in room air and alveolar breath, though they were less abundant than alkanes and were not observed as frequently (FIGS. 8–9). Ethanol was more abundant than any other alkyl alcohol, and its alveolar gradient was positive. Hence, endogenous synthesis of ethanol predominated over clearance. This finding is consistent with previous observations of endogenous ethanol in breath, where it may be a product of metabolism or bacterial fermentation in the intestine;

(Phillips M and Greenberg J: Detection of endogenous ethanol and other compounds in the breath by gas chromatography with on-column concentration of sample, Analytical Biochemistry, 1987; 163:165–169). 2-methyl alkanes ranging from C3 to C20 were also observed in room air and breath (FIGS. 10–11). The origin of these VOCs is unclear; they may be derived from methylation of alkanes.

In conclusion, these findings demonstrate that normal human breath contains a wider spectrum of alkanes, alkyl alcohols and 2-methyl alkanes than has previously been reported. Profiles of the alveolar gradients indicate that the rate of clearance (mainly by cytochrome P450) exceeded the rate of synthesis (by OFR-mediated lipid peroxidation of PUFAs) for C4 to C12 alkanes, and the rate of synthesis exceeded the rate of clearance for C13 to C20 alkanes. These findings extend the spectrum of known breath markers of oxidative stress in humans.

The Breath Alkane Profile in Breast Cancer

Breath samples were collected from a group of women undergoing screening mammography. Breath and air samples were collected and analyzed in the manner described above. This non-random sample was intentionally skewed to include a relatively large number of women with breast cancer. 35 women were studied on the same day mammography was performed, 25 with normal mammograms and 10 in whom breast cancer was detected for the first time. All diagnoses of breast cancer were subsequently confirmed by tissue biopsy. Mean alkane profiles were determined for alveolar breath (FIG. 12), room air (FIG. 13) and alveolar gradient (FIG. 14). All three curves were visibly different in women with and without breast cancer, and differences in a number of alkanes were statistically significant on t-testing. An unexpected and apparently paradoxical finding was the marked difference in composition of room air in the two groups. However, VOCs expired in the breath may modify the composition of room air, an observation which may be confirmed by the everyday experience of occupying the same room as a person with severe halitosis. The alveolar gradient curves (FIG. 14) were analyzed by logistic regression, and the posterior probability of breast cancer based upon the alkane profile alone was determined for each woman (FIG. 15). This demonstrated a clear separation between the two groups with no false positive or false negative results.

Interpretation:

The breath alkane profile of alveolar gradients was displaced downwards in women with breast cancer. This is consistent with clearance predominating over synthesis. However, the increased amount of alkanes in room air was evidence for increased synthesis of alkanes. The most likely explanation is that both synthesis and clearance of alkanes are increased in women with breast cancer, but clearance is increased to a greater extent. Displacement of the breath alkane profile was sufficient to distinguish between women with and without breast cancer with 100% sensitivity and specificity. The breath alkane profile appears to provide a rational new biomarker of breast cancer. Breath testing might provide a clinically useful new method for the early detection of breast cancer. It could be employed in mass screening because it is simpler, safer, less painful and less expensive than screening mammography.

The Breath Alkane Profile in Ischemic Heart Disease

Part A

Breath tests were performed in eight patients with unstable angina documented by coronary angiography. Their mean breath alkane profile was displaced upwards from the mean profile observed in the normal controls, consistent with an increased predominance of synthesis over clearance of alkanes. The breath test was repeated in these patients during coronary angioplasty while the balloon was inflated, and the same changes were seen in a more exaggerated form (FIG. 16). The differences between the breath alkane profiles were sufficient to distinguish between the normal controls and the patients with unstable angina with 100% sensitivity and specificity (FIG. 17).

Part B

Breath tests were performed in 19 patients with acute onset chest pain in a hospital Emergency Department. All were subsequently admitted to a cardiac care unit for treatment and further evaluation with a comprehensive battery of tests including echocardiogaphy, exercise electro-cardiography, myocardial scintigraphy and Holter monitoring. The final diagnoses in the 19 patients were unstable angina in ten, and acute myocardial infarction in nine. The results of the breath test in all patients demonstrated that the mean breath alkane profile was displaced upwards from the mean profile observed in the normal controls, consistent with an increased predominance of synthesis over clearance of alkanes (FIG. 18). The differences between the breath alkane profiles were sufficient to distinguish between the normal controls and the patients with cardiac chest pain with 100% sensitivity and specificity (FIG. 19). In addition, the differences between the breath alkane profiles were sufficient to distinguish between the patients with unstable angina and acute myocardial infarction with 100% sensitivity and specificity (FIG. 20).

Interpretation:

In the two separate pilot studies, breath tests of patients with cardiac chest pain yielded similar results: the mean breath alkane profile was displaced upwards from the mean profile observed in the normal controls, consistent with an increased predominance of synthesis over clearance of alkanes. This is consistent with myocardial ischemia causing increased OFR activity in myocardial cells. Displacement of the breath alkane profiles was sufficient to distinguish between the normal controls and the patients with cardiac chest pain with 100% sensitivity and specificity.

The Breath Alkane Profile and Alkyl Alcohol Profile in Heart Transplant Rejection Experimental methods:

Heart transplant recipients were studied at three academic program sites: Newark Beth Israel Medical Center, Newark, N.J., Mt. Sinai Medical Center, New York, and Columbia Presbyterian Medical Center, New York. 213 breath tests were performed in heart transplant patients on the same day as regular scheduled endomyocardial biopsy. Breath alkane and alkyl alcohol profiles were determined in all subjects employing the methods described above. The "gold standard" of heart transplant rejection was determined as follows: Two pathologists independently graded the degree of rejection in the endomyocardial biopsy without knowledge of each other's findings, employing a standard rating scale from 0 (no rejection) through Ia, Ib, II and IIIa (mild, moderate and severe rejection) (Billingham M E, Cary N R B, Hammond M E et al: A working formulation for the standardization of nomenclature in the diagnosis of heart and lung rejection: Heart rejection study group. J Heart Transplantation 1990; 9: 587–593). The criterion for concurrence of the two readings was that both pathologists agreed that the biopsy fell into the category of no treatment required (endomyocardial biopsy with rejection grades 0, Ia or Ib) or treatment required (endomyocardial biopsy with rejection grades II or III). Two sets of data—the breath alkane profile and the breath alkyl alcohol profile—were combined for statistical analysis by logistic regression, in order to determine the probability, based upon the breath test alone, that a patient should be assigned to the treatment or no-treatment group.

Results:

All patients recruited for the research were able to donate a breath sample into the BCA, and none reported any discomfort or adverse effects from the breath collection procedure. In summary:

1. 213 breath samples and endomyocardial biopsies were obtained.
2. The pathologists concurred on 195 endomyocardial biopsies: no treatment required in 182 and treatment required in 13.
3. The breath alkane profiles are shown in FIG. 21 for three groups: normal controls (50), heart transplant recipients requiring no treatment, and heart transplant recipients requiring treatment.
4. The breath alkyl alcohol profiles for the same three groups are shown in FIG. 22.
5. Compared to normal controls, both the breath alkane profiles and the breath alkyl alcohol profiles were significantly elevated in the heart transplant recipients.
6. Amongst the heart transplant recipients, the following alkanes were significantly increased in the group requiring treatment compared to those requiring no treatment: decane, undecane and pentadecane ($p<0.05$, 2-tailed t-test).
7. Amongst the heart transplant recipients, the following alkyl alcohols were significantly increased in the group requiring treatment compared to those requiring no-treatment: hexadecanol and heptadecanol ($p<0.01$, 2-tailed t-test).
8. Logistic regression analysis of the breath alkane profiles combined with the breath alkyl alcohol profiles separated the heart transplant recipients requiring no treatment from those requiring treatment. The receiver operating characteristic (ROC) curve is shown in FIG. 23. At the shoulder of the curve, the breath test was 84.6% sensitive and 80.2% specific.

Conclusions:
1. In heart transplant recipients, the combination of the breath alkane profile and the breath alkyl alcohol profile distinguished with high sensitivity and specificity between those with low-grade rejection requiring no treatment and those with higher grade rejection requiring treatment.
2. The difference between the two groups appeared to result from differences in the relative severity of oxidative stress.
3. Oxidative stress appeared to be increased in all heart transplant recipients, regardless of the state of rejection activity on the endomyocardial biopsy.

TABLE 1

BREATH VOCs RANKED BY FREQUENCY OF OCCURENCE

| VOC | Mean alveolar gradient | % subjects |
|---|---|---|
| 50 most frequently occurring VOCs with positive alveolar gradients | | |
| Isoprene | 60.34 | 100 |
| Benzene, (1-methylethenyl)- | 4.77 | 100 |
| Naphthalene | 4.07 | 100 |
| 2.5-Cyclohexadiene-1,4-dione, 2,6-bis(1,1-dimethylethyl)- | 0.61 | 100 |
| Naphthalene, 1-methyl- | 0.54 | 100 |
| Butane, 2-methyl- | 0.33 | 100 |
| Tetradecane | 0.23 | 100 |
| Pentadecane | 0.13 | 100 |
| Dodecane | 0.02 | 100 |
| Benzothiazole | 0.93 | 98 |
| 1,1'-Biphenyl, 2.2'-diethyl- | 0.69 | 98 |
| Ethane, 1,1,1-trichloro- | 0.12 | 98 |
| Tridecane | 0.10 | 98 |
| Styrene | 1.00 | 96 |
| Benzene, 1-methyl-4-(1-methylethyl)- | 0.01 | 96 |
| Ethanone, 1 phenyl- | 1.49 | 94 |
| Acetone | 27.91 | 92 |
| Benzenemethanol, .alpha.,.alpha.-dimethyl- | 20.39 | 92 |
| beta-Myrcene | 0.05 | 92 |
| Phenol, 2.6-bis(1,1-dimethylethyl)-4-methyl- | 0.34 | 90 |
| 1H-Indene, 2.3-dihydro-1,6-dimethyl- | 0.01 | 84 |
| 1,1'-Biphenyl | 0.06 | 78 |
| Ethene, tetrachloro- | 7.70 | 76 |
| 2.5-Cyclohexadiene-1,4-dione, 2.5-bis(1.1-dimethylpropyl)- | 0.24 | 74 |
| Octane, 2.6 thimethyl- | 0.02 | 74 |
| Benzoic acid, 4-ethoxy-, ethyl ester | 0.30 | 70 |
| Pentane, 3 methylene- | 0.28 | 70 |
| (1.1-Bicyclopentyl)-2-one | 2.63 | 68 |
| all Limonene | 1.79 | 68 |
| Hexane, 2,2.5 thimethyl- | 0.36 | 66 |
| 1H-Indene, 2,3-dihydro-4,6-dimethyl- | 0.15 | 64 |
| 2 Butene, 2,3 dimethyl- | 0.25 | 64 |
| Benzene, 1 bromo-3,Huoro- | 0.12 | 64 |
| Naphthalene, 2,7-dimethyl- | 0.09 | 64 |
| Naphthalene, 2-methyl- | 0.32 | 64 |
| Hexadecane, 2,6,10,14-tetramethyl- | 0.16 | 62 |
| 2 beta-Pinene | 0.58 | 60 |
| Acetic acid | 2.63 | 60 |
| Propanoic acid, 2 methyl-, 1-(1,1-dimethylethyl)-2-methyl-1,3-propanediyl ester | 0.21 | 60 |
| 1.2 Benzenedicarboxylic acid, diethyl ester | 0.06 | 58 |
| Endobornylacetate | 0.42 | 58 |
| Benzene, (3 methyl-2-butenyl)- | 0.13 | 56 |
| Naphthalene, 1 ethyl- | 0.05 | 56 |
| Naphthalene, 2 ethyl- | 0.00 | 56 |
| Benzene, 1 ethyl-4-(1-methylethyl)- | 0.02 | 54 |
| Benzene, butyl- | 0.41 | 54 |
| Cyclohexene | 0.05 | 54 |
| Naphthalene, 1,6-dimethyl- | 0.11 | 54 |
| Nonanal | 0.32 | 54 |
| 2 Propanoic acid, 2 methyl-, 1,2-ethanedrylbistoxy-2,1-ethanediyl) ester | 12.47 | 52 |
| Octadecane | 0.27 | 52 |
| Octane, 2.5 dimethyl- | 0.10 | 52 |
| 50 most frequently occurring VOCs with negative alveolar gradients | | |
| Benzene | −0.48 | 100 |
| Benzene, 1-ethyl-2-methyl- | −10.09 | 100 |
| Benzene, ethyl- | −1.73 | 100 |
| Benzene, methyl- | −7.27 | 100 |
| Benzene, propyl- | −1.72 | 100 |
| Cyclohexane, methyl- | −0.75 | 100 |
| Decane | −0.28 | 100 |
| Heptane | −1.25 | 100 |
| Heptane, 2-methyl- | −0.89 | 100 |
| Heptane, 3-methyl- | −0.83 | 100 |
| Hexane | −0.79 | 100 |
| Hexane, 3-methyl- | −1.02 | 100 |
| Nonane | −0.44 | 100 |
| Pentane, 2,3,4-trimethyl- | −0.26 | 100 |
| Pentane, 2-methyl- | −0.43 | 100 |
| Pentane, 3-methyl- | −0.59 | 100 |
| Propane, 2-methoxy-2-methyl- | −9.44 | 100 |
| Undecane | −0.52 | 100 |
| alpha-Pinene, (1)- | −0.06 | 98 |
| Cyclohexane, ethyl- | −0.33 | 98 |
| Cyclopentane, methyl- | −1.25 | 98 |
| Decanal | 0.00 | 98 |
| 1-Pentene, 2-methyl- | −0.21 | 96 |
| Benzene, 1,2,3,5-tetramethyl- | −0.51 | 96 |
| Pentane, 2,3,3-trimethyl- | −0.10 | 96 |
| 1H-Indene, 2,3-dihydro-4,7-dimethyl- | −0.29 | 94 |
| Benzaldehyde | −0.31 | 94 |
| Camphene | −0.20 | 94 |
| Cyclopentane, 1,3-dimethyl-, cis- | −0.31 | 94 |
| Cyclopentane, ethyl- | −0.29 | 94 |
| Cyclopentene | −0.13 | 94 |

TABLE 1-continued

BREATH VOCs RANKED BY FREQUENCY OF OCCURENCE

| VOC | Mean alveolar gradient | % subjects |
|---|---|---|
| 1H-Indene, 2,3-dihydro-5-methyl- | −0.30 | 92 |
| Benzene, 1,2,4-trimethyl- | −6.89 | 92 |
| Benzene, 1,3-dimethyl- | −5.38 | 92 |
| Benzene, 1-methyl-3-propyl- | −0.21 | 92 |
| Butane | −0.52 | 92 |
| Octane, 3-methyl- | −0.26 | 92 |
| Benzene, 1,2,3,4-tetramethyl- | −0.22 | 90 |
| Cyclohexane, 1,3-dimethyl-, cis- | −0.31 | 90 |
| Hexene, 2-methyl- | −1.48 | |
| 2-Hexene, (E)- | −0.27 | 88 |
| Benzene, (1-methylethyl)- | −0.76 | 88 |
| Benzene, 1,4-dimethyl- | −4.95 | 88 |
| Benzene, 1-ethyl-2,3-dimethyl- | −0.53 | 88 |
| Butane, 2,3-dimethyl- | −0.10 | 88 |
| Benzene, 1,3,5-trimethyl- | −2.44 | 86 |
| Benzene, 4-ethyl-1,2-dimethyl- | −0.71 | 86 |
| Heptane, 2,4-dimethyl- | −0.05 | 86 |
| Heptane, 2,5-dimethyl- | −0.20 | 84 |
| Hexane, 2,4-dimethyl- | −0.99 | 82 |

TABLE 2

BREATHE VOCs RANKED BY ABUNDANCE

| 'OC | Mean alveolar gradient | % subjects |
|---|---|---|
| 50 VOCs with highest mean positive alveolar gradients | | |
| 4,5-Dimorpholino-2-methoxy-6-phenylpyrimidine | 655.61 | 4 |
| (4,4-D2)-15,16-Dimethoxyetythrinan-7,8-dion-enol | 162.20 | 2 |
| Cyclohexanol, 5-methyl-2-(1-methylethyl)- | 75.83 | 4 |
| Isoprene | 60.34 | 100 |
| Methanol | 28.90 | 2 |
| Acetone | 27.91 | 92 |
| Benzenemethanol, .alpha.,.alpha.-dimethyl- | 20.39 | 92 |
| L Menthalone | 13.64 | 20 |
| Encosane, 9-octyl- | 12.60 | 2 |
| 2H-1,4-Benzodiazepin-2-one, 7-chloro-1,3-dihydro-5-phenyl-1-(trimethylsilyl)- | 12.49 | 18 |
| 2 Propenoic acid, 2-methyl-, 1,2-ethanediylbistoxy-2,1-ethanediyl) ester | 12.47 | 52 |
| Menthol | 7.82 | 2 |
| Ethene, tetrachloro- | 7.70 | 76 |
| (1)-Menthylacetate | 6.92 | 2 |
| 1,8-Cineole | 6.39 | 14 |
| Oxetane, 2 ethyl-3-methyl- | 5.02 | 6 |
| Benzene, (1-methylethenyl)- | 4.77 | 100 |
| Pryazine, 2-ethyl-3-methyl- | 4.11 | 2 |
| Naphthalene | 4.07 | 100 |
| 1H-1,2,4-Triazol-3-amine | 3.79 | 18 |
| Propanoic acid, 2-methyl-, 3-hydroxy-2,4,4-trimethylpentyl ester | 3.72 | 2 |
| Cyclopropane, (1-methylethyl)- | 3.59 | 2 |
| Methane, trichlorolluoro- | 3.45 | 40 |
| 2 Methyl 5 propylpyrazine | 3.18 | 2 |
| Benzene, (2-methyl-1-methylenepropyl)- | 3.11 | 4 |
| Cyclopentanone | 3.07 | 34 |
| Cyclohexane, methoxy- | 2.81 | 4 |
| 50 VOCs with the highest mean negative alveolar gradients | | |
| (1.1'-Bicyclopentyl)-2-one | 2.63 | 68 |
| Acetic acid | 2.63 | 60 |
| Butanoic acid, butyl ester | 2.44 | 2 |
| 2-Propenoic acid, 2-methyl-, 1,2-ethanediyl ester | 2.39 | 48 |
| Acetic acid, (bis)(trimethylsilyl)oxylphosphinyl)-, trimethylsilyl ester | 2.28 | 40 |
| Huourea | 2.16 | 4 |
| Cyclopentane, (1-methylethyl)- | 2.15 | 2 |

TABLE 2-continued

BREATHE VOCs RANKED BY ABUNDANCE

| 'OC | Mean alveolar gradient | % subjects |
|---|---|---|
| 1,3,7-Octatriene, 3,7-dimethyl- | 2.13 | 2 |
| 2-(1-Methylpropyl)pyrazine | 2.09 | 2 |
| Hexadecanoic acid, 1-methylethyl ester | 2.08 | 4 |
| Linalool | 2.06 | 12 |
| Luran, 2-butyltetrahydro- | 1.95 | 6 |
| Cyclohexanol, 2-amino-, cis- | 1.93 | 6 |
| 1,3-Propanediol, 2-methyl-2-propyl- | 1.91 | 36 |
| 1,E-11,Z-13-Hexadecatriene | 1.85 | 2 |
| 9 Homonoradamant-9-ene | 1.85 | 2 |
| Peroxydihydrocostunolide | 1.83 | 4 |
| Henercosane | 1.80 | 8 |
| all Limonene | 1.79 | 68 |
| Pyrazine, 2,3 dimethyl- | 1.77 | 2 |
| 1 Propene, 1-(methylthio)-, (E)- | 1.75 | 16 |
| 1 Propanol, 2,2-dimethyl- | 1.73 | 2 |
| Bicyclo(4 1 0)heptane, 3,7,7-trimethyl- | 1.71 | 2 |
| 2-Propanol | −61.41 | 28 |
| 1-Propene | −27.15 | 2 |
| Benzene, 1-ethyl-2-methyl- | −10.09 | 100 |
| Propane, 2-methoxy-2-methyl- | −9.44 | 100 |
| Octane, 3,4-dimethyl- | −8.91 | 2 |
| Benzene, methyl- | −7.27 | 100 |
| Cyclohexene, 1-methyl-4-(1-methylethyl)-,(R)- | −7.17 | 58 |
| Benzene, 1,2,4-trimethyl- | −6.89 | 92 |
| 4-Penten-2-ol | −6.42 | 2 |
| Benzene, 1,3-dimethyl- | −5.38 | 92 |
| 3-Butenoic acid | −5.34 | 2 |
| Benzene, 1,4-dimethyl- | −4.95 | 88 |
| 2-Chloro-4-(4-methoxyphenyl)-6-(4-nitrophenyl)pyrimidine | −4.30 | 18 |
| Pentane | −3.95 | 44 |
| Cyclohexanol, 5-methyl-2-(1-methylethyl)-, (1.alpha.,2,beta.,5,alpha.)-(.+-.)- | −3.30 | 2 |
| Hexanol-4-D2 | −2.85 | 4 |
| 1 Butene, 2-methyl- | −2.72 | 78 |
| Octane, trimethyl- | −2.68 | 2 |
| Benzene, 1,3,5-trimethyl- | −2.44 | 86 |
| (thanone, 1-(3-ethylcyclobutyl)- | −2.31 | 2 |
| Pyrrolidine | −2.24 | 6 |
| Xylene | −2.14 | 32 |
| Octane | −2.02 | 74 |
| 3,4-Dihydropyran | −1.82 | 2 |
| Undecane, 3,5-dimethyl- | −1.75 | 6 |
| Benzene, 1-methyl-2-propyl- | −1.75 | 76 |
| alpha-Ylangene | −1.73 | 2 |
| Benzene, ethyl- | −1.73 | 100 |
| Benzene, propyl- | −1.72 | 100 |
| Methane, dichloro- | −1.71 | 10 |
| 1-Butene, 2,3-dimethyl- | −1.69 | 48 |
| 1,2-Pentadiene | −1.65 | 2 |
| Benzene, 1-methyl-4-propyl- | −1.60 | 10 |
| Phosphonic acid, diphenyl ester | −1.60 | 2 |
| Heptadecane, 9-octyl- | −1.58 | 4 |
| 1 Octadecene | −1.54 | 4 |
| Bicyclol3,2.1loci-2-ene, 3-methyl-4-methylene- | −1.51 | 2 |
| Pentane, 2,2,3,4-tetramethyl- | −1.51 | 28 |
| 4-Heptanone, 3-methyl- | −1.48 | 4 |
| Hexane, 2-methyl- | −1.48 | 90 |
| 3 lodo-thiophene-2-carboxamide | −1.47 | 2 |
| 1 R-Methyl-2T-phenylcyclopropane | −1.41 | 6 |
| Benzene, 1,2,3-trimethyl- | −1.39 | 56 |
| Palmitic acid, 2-(trimethylsiloxyl)ethyl ester | −1.34 | 2 |
| beta-Ocimene-x | −1.32 | 8 |
| 4-Hydroxy-2-isopropyl-4,7-dimethyl-1(4H)-naphthalenone | −1.31 | 2 |
| 7-Azabicyclol4 1.0thepiane, 3-methyl- | −1.31 | 2 |
| 4.7-Diphenyl-6-hydroxymethyl-1,2,5-oxadiazolol3.4-clpyridine | −1.27 | 2 |
| Benzene, 2-ethyl-1,3-dimethyl- | −1.26 | 54 |
| 2 Butanol, 3-methyl- | −1.26 | 2 |

| Appendix 1: Kinetic Analysis of Determinants of the Alveolar Gradient | |
|---|---|
| Let  R | = rate of movement of VOC (mol/min) |
| C | = concentration of VOC (mol/l) |
| RMV | = respiratory minute volume (l/min) |
| Al equilibrium: $R_{in\ to\ body}$ | = $R_{out\ of\ body}$ |
| $R_{pulmonary\ input} + R_{extra\ pulmonary\ input}$ | = $R_{pulmonary\ output} + R_{clearance}$ |
| $R_{extra\ pulmonary\ input} - R_{clearance}$ | = $R_{pulmonary\ output} - R_{pulmonary\ input}$ |
|  | = $(C_{alveolar\ breath} - C_{room\ on}) \times RMV$ |
| ie alveolar gradient | = $C_{alveolar\ breath} - C_{room\ on}$ |
|  | = $\dfrac{(R_{extra\ pulmonary\ input} - R_{clearance})}{RMV}$ |
| For a VOC synthesized in body and not ingested from extra pulmonary sources | |
| $R_{extra\ -\ pulmonary\ input}$ | = $R_{synthesis}$ |
| Hence alveolar gradient | = $\dfrac{(R_{synthesis} - R_{clearance})}{RMV}$ |

What is claimed is:

1. A process for determining the presence or absence of disease in a mammal, including a human, which comprises;

collecting a representative sample of alveolar breath from the mammal;

collecting a representative sample of ambient air;

analyzing the samples of breath and air to determine content of n-alkanes having 2 to 20 carbon atoms, inclusive;

calculating alveolar gradients of the n-alkanes having 2 to 20 carbon atoms, inclusive, in the breath sample in order to determine an alkane profile; and comparing the alkane profile to baseline alkane profiles calculated for mammals known to be free of the disease to be determined with a finding of differences in the alkane profile from the baseline alkane profile being indicative of the presence of the disease.

2. The process of claim 1 wherein the disease is breast cancer.

3. The process of claim 1 wherein the disease is manifested by cardiac chest pain.

4. The process of claim 1 wherein the mammal is a human.

5. The process of claim 1 wherein the disease is unstable angina pectoris.

6. The process of claim 1 wherein the disease is acute myocardial infarction.

7. The process of claim 1 wherein the disease is renal disease.

8. A process for determining the presence of breast cancer in a human, which comprises;

collecting a representative sample of alveolar breath from a human;

collecting a representative sample of ambient air;

analyzing the collected samples of breath and of air to determine content of n-alkanes having 2 to 20 carbon atoms, inclusive;

calculating alveolar gradients of the n-alkanes having 2 to 20 carbon atoms, inclusive, in the breath sample in order to determine an alkane profile;

calculating a baseline alkane profile for humans known to be free of breast cancer; and comparing the alkane profile to the baseline alkane profile with a finding of downward displacement in the alkane profile from the baseline alkane profile being indicative of the presence of breast cancer.

9. A process for determining the presence of ischemic heart disease in a human, which comprises;

collecting a representative sample of alveolar breath from a human;

collecting a representative sample of ambient air;

analyzing the collected samples of breath and of air to determine content of n-alkanes having 2 to 20 carbon atoms, inclusive;

calculating alveolar gradients of the n-alkanes having 2 to 20 carbon atoms, inclusive, in the breath sample, in order to determine an alkane profile;

calculating a baseline alkane profile for humans known to be free of ischemic heart disease;

comparing the alkane profile to the baseline alkane profile with a finding of upward displacement in the alkane profile from the baseline alkane profile being indicative of the presence of ischemic heart disease.

10. A process for determining the presence of renal disease in a human, which comprises;

collecting a representative sample of alveolar breath from a human;

collecting a representative sample of ambient air;

analyzing the collected samples of breath and of air to determine content of n-alkanes having 2 to 20 carbon atoms, inclusive;

calculating alveolar gradients of the n-alkanes having 2 to 20 carbon atoms, inclusive, in the breath sample in order to determine an alkane profile;

calculating a baseline alkane profile for humans known to be free of renal disease; and comparing the alkane profile to the baseline alkane profile with a finding of downward displacement in the alkane profile from the baseline alkane profile being indicative of the presence of renal disease.

* * * * *